United States Patent
Gundlapalli et al.

(10) Patent No.: US 6,355,045 B1
(45) Date of Patent: Mar. 12, 2002

(54) METHOD AND APPARATUS FOR SURGICALLY PREPARING A TIBIA FOR IMPLANTATION OF A PROSTHETIC IMPLANT COMPONENT WHICH HAS AN OFFSET STEM

(75) Inventors: Ramarao V. Gundlapalli, Leesburg, IN (US); Wayne M. Goldstein, Highland Park, IL (US); Donald Marcoccio, Fort Wayne, IN (US); Diana McCue, Pocasset, MA (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/750,930

(22) Filed: Dec. 28, 2000

(51) Int. Cl.$^7$ ................................................ A61B 17/56
(52) U.S. Cl. ............................... 606/88; 606/86; 606/87
(58) Field of Search ............................... 606/80, 79, 78, 606/88, 84, 85, 86, 87, 102, 170, 180, 167, 159, 172; 623/20.15, 20.32

(56) References Cited

U.S. PATENT DOCUMENTS

| | | | |
|---|---|---|---|
| 5,613,970 A | * | 3/1997 | Houston et al. ............... 606/88 |
| 5,634,927 A | * | 6/1997 | Houston et al. ............... 606/80 |
| 5,690,636 A | * | 11/1997 | Wildgoose et al. |
| 5,733,290 A | * | 3/1998 | McCue et al. ............... 606/86 |
| 5,976,147 A | * | 11/1999 | Lasalle et al. ................ 606/88 |
| 6,159,216 A | * | 12/2000 | Burkinshaw et al. ......... 606/88 |
| 6,228,091 B1 | * | 5/2001 | Lombardo et al. ............ 606/88 |

* cited by examiner

*Primary Examiner*—Pedro Philogene
(74) *Attorney, Agent, or Firm*—Maginot, Addison & Moore

(57) ABSTRACT

A surgical assembly for preparing a tibia for implantation of a prosthetic implant includes a tray trial adapted to be secured to a proximal end of the tibia. The tray trial includes a plate having a plate opening defined therein. The plate opening has a center point. The surgical assembly also includes a first guide adapted to be secured to the tray trial. The first guide has a guide opening defined therein. The guide opening has a first bushing-receiving portion and a second bushing-receiving portion which is distinct from the first bushing-receiving portion. The surgical assembly also includes a drill bushing positionable in either the first bushing-receiving portion of the guide opening or the second bushing-receiving portion of the guide opening. The drill bushing has a bushing bore extending therethrough. The bushing bore has a center point. The center point of the bushing bore of the drill bushing is offset from the center point of the plate opening of the tray trial in a first direction when the drill bushing is positioned in the first bushing-receiving portion of the guide opening. The center point of the bushing bore of the drill bushing is offset from the center point of the plate opening of the tray trial in a second direction when the drill bushing is positioned in the second bushing-receiving portion of the guide opening. A method of surgically preparing a tibia for implantation of a prosthetic implant is also disclosed.

17 Claims, 23 Drawing Sheets

METHOD AND APPARATUS FOR SURGICALLY PREPARING A TIBIA FOR IMPLANTATION OF A PROSTHETIC IMPLANT COMPONENT WHICH HAS AN OFFSET STEM

TECHNICAL FIELD OF THE INVENTION

The present invention relates generally to a surgical instrument assembly, and more particularly to a method and apparatus for surgically preparing a tibia for implantation of a prosthetic implant component which has an offset stem.

BACKGROUND OF THE INVENTION

During the lifetime of a patient, it may be necessary to perform a joint replacement procedure on the patient as a result of, for example, disease or trauma. One such type of joint replacement procedure is a total knee replacement procedure in which a diseased and/or damaged knee joint is replaced with a prosthetic knee joint. A typical total knee replacement procedure utilizes a prosthesis which generally includes a femoral component, a tibial tray, and a tibial bearing insert. The femoral component generally includes a pair of laterally spaced apart condylar portions, the distal surfaces of which bear against a complementary pair of surfaces defined in the tibial bearing insert. The tibial tray typically includes a plate having a stem extending distally therefrom. The stem is implanted in a prepared medullary canal of the patient's tibia. Once implanted in such a manner, the tibial tray provides a surface on the proximal end of the tibia to which the tibial bearing insert may be affixed.

During performance of such a knee replacement procedure, the surgeon must evaluate the size and condition of the patient's bones (e.g. the patient's tibia) in order to determine the proper type and configuration of each of the various types of prosthetic components which are to be implanted. Moreover, the patient's bones must also be surgically prepared to a condition in which the prosthetic components may be implanted. Both proper surgical preparation of the bones and proper component selection are critical to the success of the procedure.

One condition which renders surgical preparation relatively difficult is the case in which the tibial canal of the patient's tibia is offset from, or otherwise not coincident with, the center of the tibia. Indeed, it is known that the anatomy of some patients may create a situation in which the tibial canal of the patient's tibia is offset from the center of the tibia by as much as three to four millimeters (3–4 mm). Such an offset is above and beyond a slight anterior-posterior offset of the tibial canal which is inherent in most patient's anatomies. It should be appreciated that if a tibial implant having a stem which is centered relative to the implant's plate is implanted into a patient's tibia which has an offset tibial canal, undesirable impingement of the stem into contact with the cortical bone of the tibia may result.

As a result of these problems, a number of tibial components have heretofore been designed which include stems that are offset relative to the plate of the component. However, heretofore designed instruments for implanting such offset tibial components have often been difficult to use and often create a degree of uncertainty for the surgeon in regard to the positioning of the implant relative to the tibia.

What is needed therefore is a surgical instrument assembly which overcomes one or more of the above-mentioned drawbacks. What is particularly needed is a surgical instrument assembly which may be utilized to quickly, reproducibly, and accurately surgically prepare the tibia for implantation of a tibial component which has an offset stem.

SUMMARY OF THE INVENTION

In accordance with one embodiment of the present invention, there is provided a surgical assembly for preparing a tibia for implantation of a prosthetic implant. The surgical assembly includes a tray trial adapted to be secured to a proximal end of the tibia. The tray trial includes a plate having a plate opening defined therein. The plate opening has a center point. The surgical assembly also includes a first guide adapted to be secured to the tray trial. The first guide has a guide opening defined therein. The guide opening has a first bushing-receiving portion and a second bushing-receiving portion which is distinct from the first bushing-receiving portion. The surgical assembly also includes a drill bushing positionable in either the first bushing-receiving portion of the guide opening or the second bushing-receiving portion of the guide opening. The drill bushing has a bushing bore extending therethrough. The bushing bore has a center point. The center point of the bushing bore of the drill bushing is offset from the center point of the plate opening of the tray trial in a first direction when the drill bushing is positioned in the first bushing-receiving portion of the guide opening. The center point of the bushing bore of the drill bushing is offset from the center point of the plate opening of the tray trial in a second direction when the drill bushing is positioned in the second bushing-receiving portion of the guide opening.

In accordance with another embodiment of the present invention, there is provided a method of surgically preparing a tibia for implantation of a prosthetic implant. The method includes the step of securing a tray trial to a proximal end of the tibia. The tray trial includes a plate having a plate opening defined therein. The plate opening has a center point. The method also includes the step of securing a first guide to the tray trial. The first guide has a guide opening defined therein. The guide opening has a first bushing-receiving portion and a second bushing-receiving portion which is distinct from the first bushing-receiving portion. The method also includes the step of determining if a first drilled hole is to be offset in either a first direction or a second direction from the center point of the plate opening. The method also includes the step of positioning a drill bushing in either the first bushing-receiving portion of the guide opening or the second bushing-receiving portion of the guide opening based on the determining step. The drill bushing has a bushing bore extending therethrough. The bushing bore has a center point. The center point of the bushing bore of the drill bushing is offset from the center point of the plate opening of the tray trial when the drill bushing is positioned in either the first bushing-receiving portion of the guide opening or the second bushing-receiving portion of the guide opening.

It is therefore an object of the present invention to provide a new and useful surgical assembly for preparing a tibia for implantation of a prosthetic implant.

It is moreover an object of the present invention to provide an improved surgical assembly for preparing a tibia for implantation of a prosthetic implant.

It is a further object of the present invention to provide a new and useful method of surgically preparing a tibia for implantation of a prosthetic implant.

It is also an object of the present invention to provide an improved method of surgically preparing a tibia for implantation of a prosthetic implant.

It is yet another object of the present invention to provide a surgical instrument assembly which may be utilized to quickly, reproducibly, and accurately surgically prepare the tibia for implantation of a tibial component which has an offset stem.

DETAILED DESCRIPTION OF THE INVENTION

Figure 1:
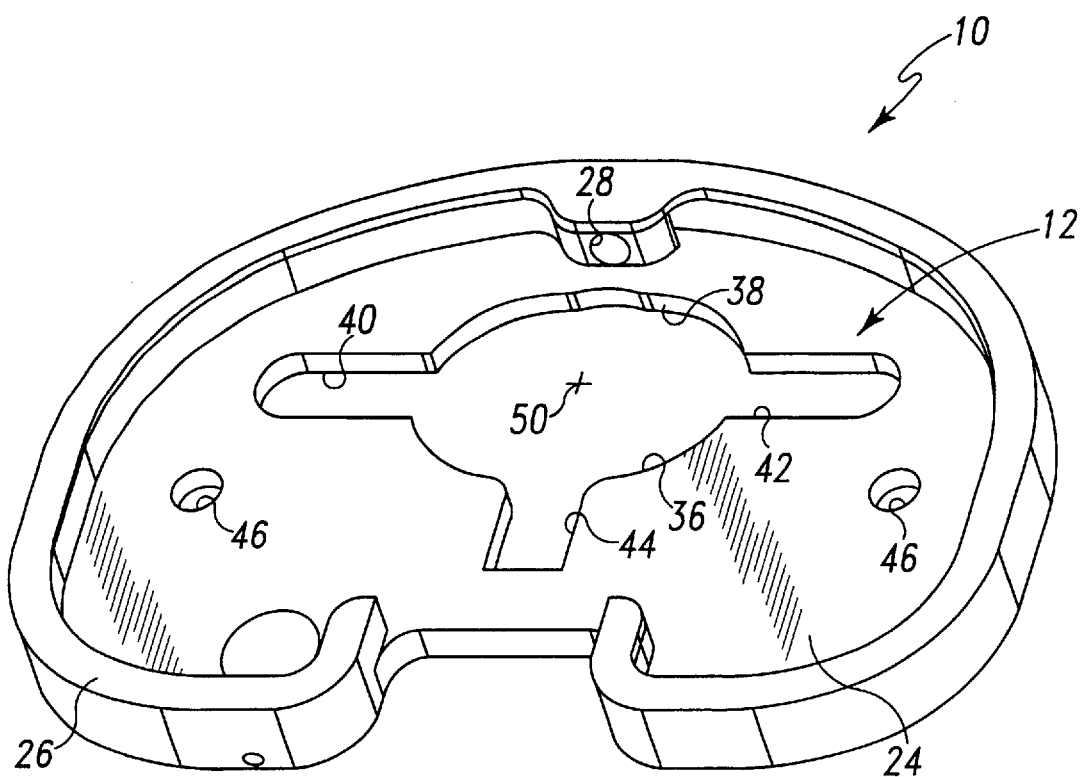
FIG. 1 is a perspective view of a tray trial which incorporates the features of the present invention therein.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIGS. 1–12, there is shown a surgical instrument assembly 10 for use during performance of a joint replacement procedure such as a total knee replacement procedure. It should be appreciated that although the present invention is herein exemplarily described in regard to performance of a total knee replacement procedure, certain of the concepts of the present invention may be utilized in regard to replacement procedures at numerous other joint locations throughout the body.

Figure 6:
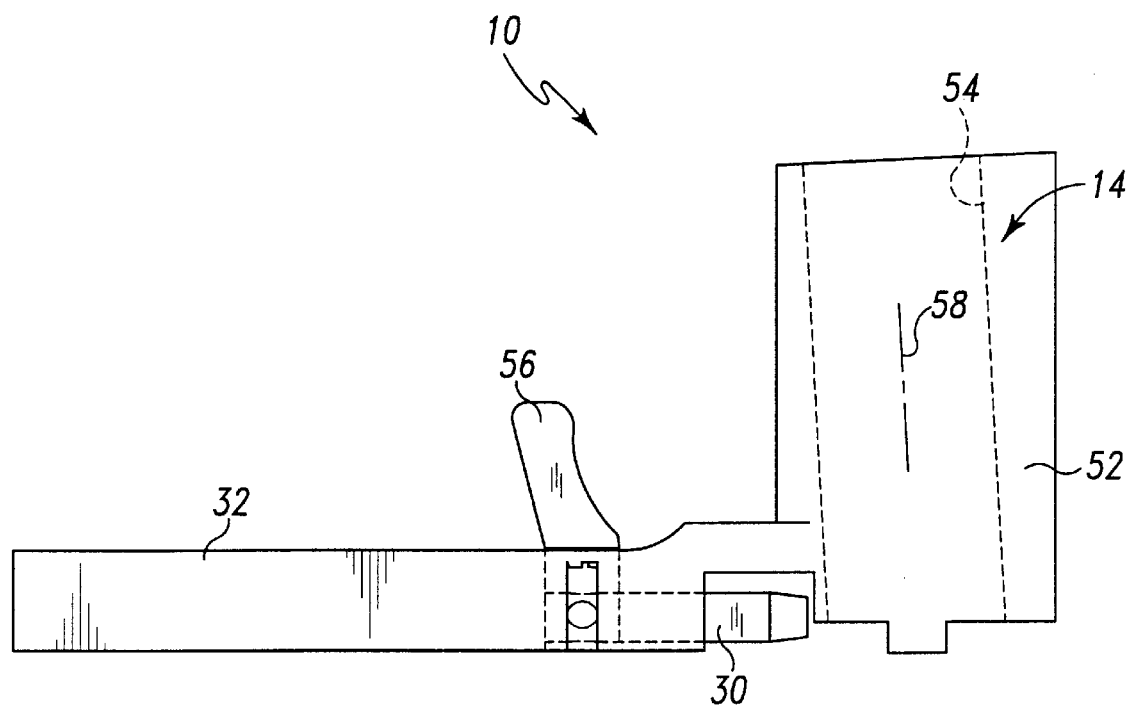
FIG. 6 is a side elevational view of the drill guide of FIG. 4.
Figure 7:
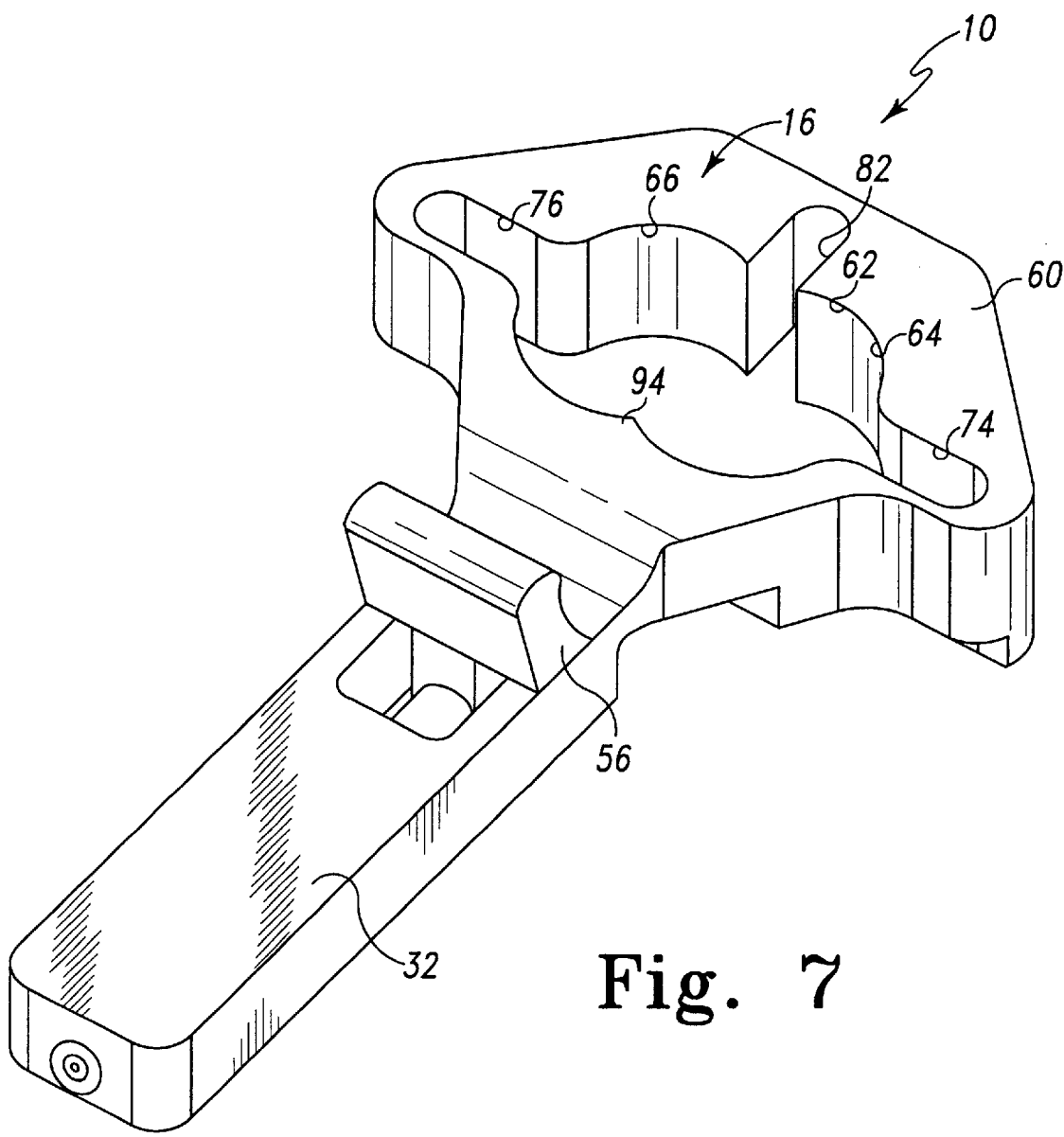
FIG. 7 is a perspective view of a drill/broach guide which incorporates the features of the present invention therein.
Figure 8:
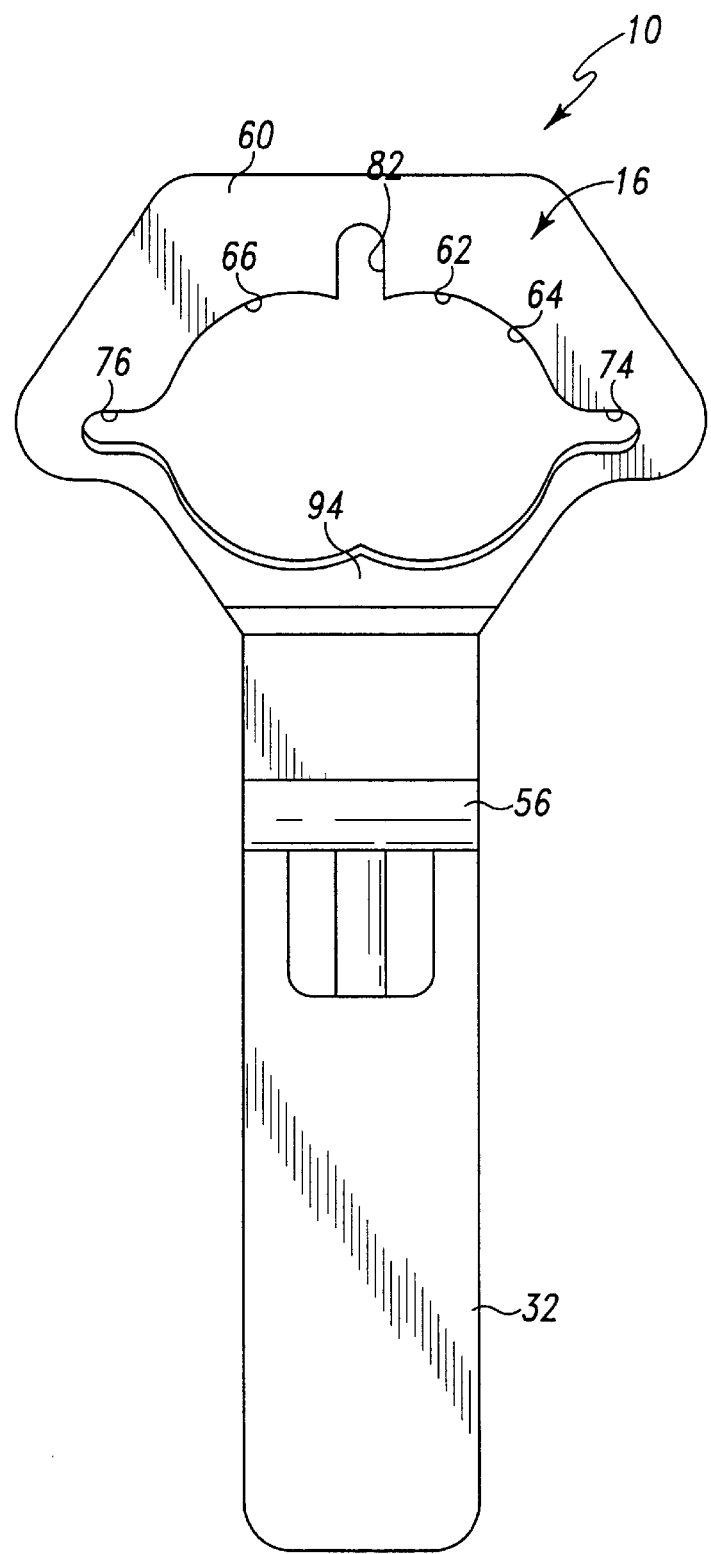
FIG. 8 is a top elevational view of the drill/broach guide of FIG. 7.
Figure 9:
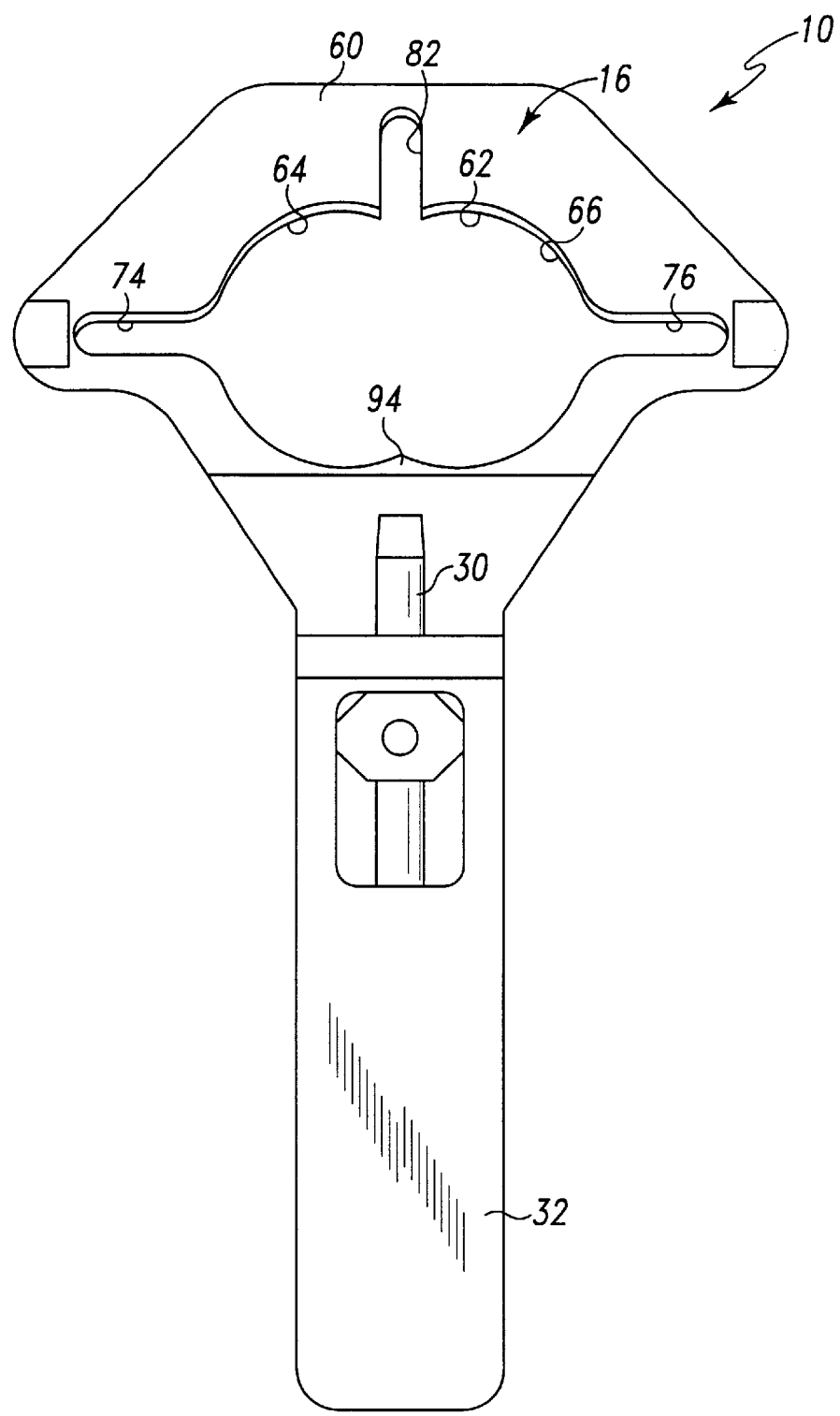
FIG. 9 is a bottom elevational view of the drill/broach guide of FIG. 7.

The instrument assembly 10 includes a tray trial 12 (see FIGS. 1–3), a drill guide 14 (see FIGS. 4–6), and a drill/broach guide 16 (see FIGS. 7–9). As shall be discussed below in greater detail, the instrument assembly 10 is utilized to surgically prepare a proximal end 18 of a patient's tibia 20 (see FIG. 23) for implantation of an implant such as an offset tibial component 100 (see FIGS. 13 and 14). The tray trial 12 includes a plate 24 which has a rim 26 secured around the periphery thereof. The rim 26 has a pin receiving aperture 28 defined therein. The pin receiving aperture 28 is configured to receive a locking pin 30 associated with a number of handle assemblies 32 associated with the instrument assembly 10. For example, a detachable handle assembly 32 may be secured to the tray trial 12 as shown in FIG. 15 in order to allow the surgeon to quickly and easily adjust the position of the tray trial 12 over the proximal tibia 18. Moreover, as shown in FIGS. 5, 9, 18, and 20, the drill guide 14 and the drill/broach guide 16 may be configured to include an integrated handle assembly 32. In such a configuration, the locking pin 30 of the handle assembly 32 associated with the drill guide 14 or the drill/broach guide 16 is received into the pin receiving aperture 28 in order to secure the guide 14 or 16 to the rim 26 and hence the tray trial 12.

Figure 2:
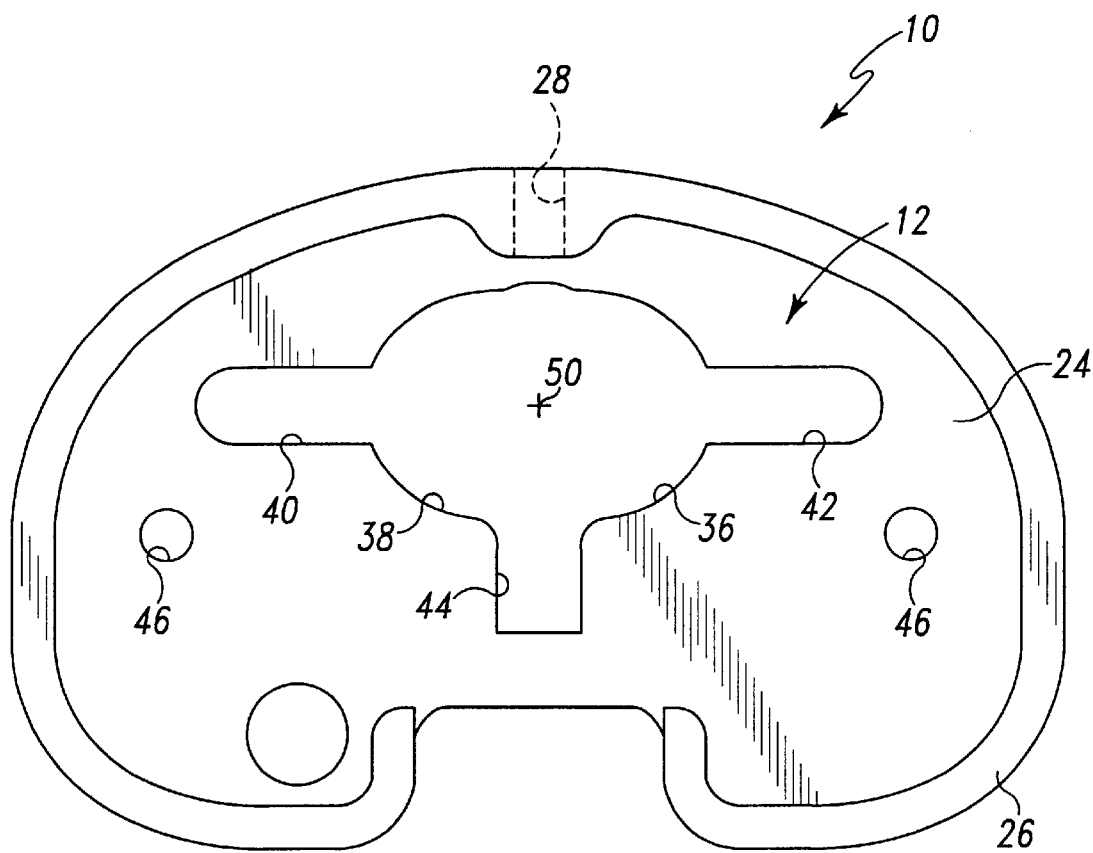
FIG. 2 is a top elevational view of the tray trial of FIG. 1.
Figure 3:
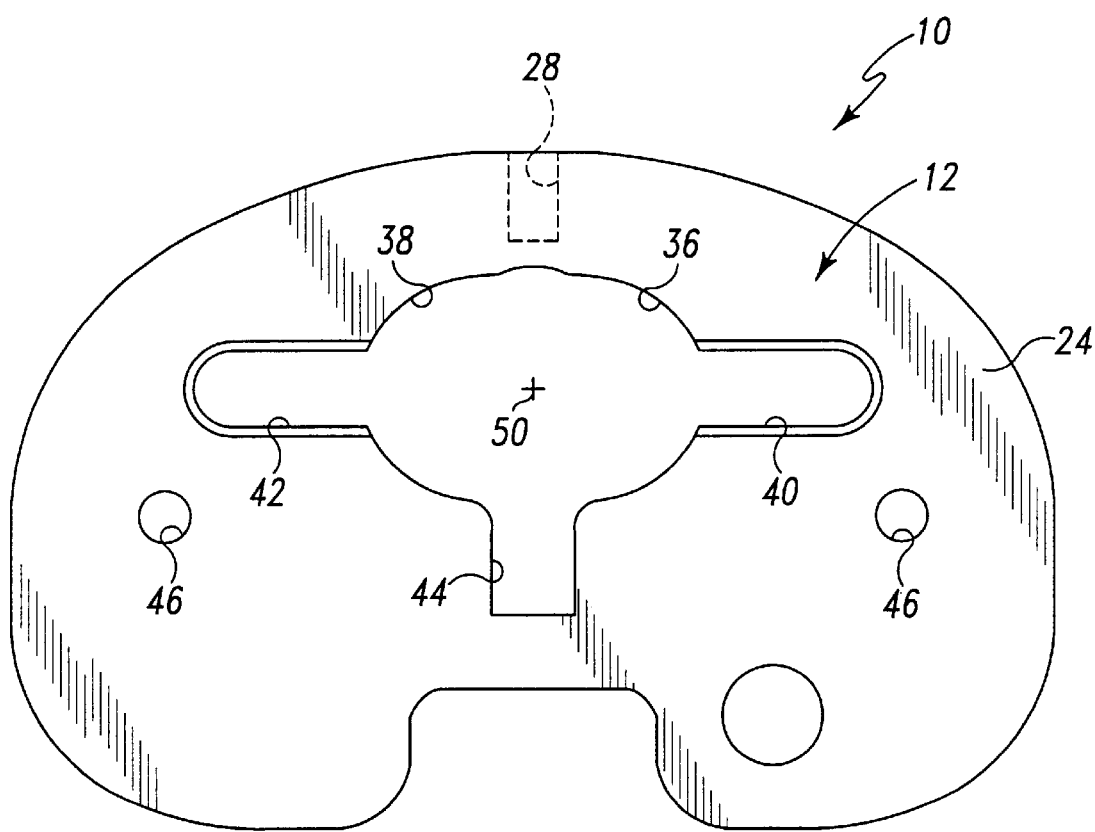
FIG. 3 is a bottom elevational view of the tray trial of FIG. 1.

The plate 24 of the tray trial 12 has a plate opening 36 defined therein. As shown in FIGS. 1–3, the plate opening 36 has an oblong-shaped central portion 38 with a number of extension portions 40, 42, 44 extending outwardly therefrom. As will be discussed below in greater detail, the configuration of the plate opening 36 allows for the advancement of various bone drills and broaches into the proximal end 18 of the tibia 20 without the need to detach the tray trial 12 from the proximal end 18 of the tibia 20. As shown in FIGS. 2 and 3, the plate opening 36 has a center point 50 which is the center of the oblong-shaped central portion. The center point 50 corresponds approximately to the center of the proximal end 18 of the patient's tibia 20 when the tray trial 12 is centered on the same or adjusted to obtain desired coverage of the proximal end 18 by the tray trial 12.

The plate 24 of the tray trial 12 also has a number of fastener openings 46 defined therein. The fastener openings 46 are provided to receive a number of fasteners such as fixation pins 48 (see FIG. 17) which are utilized to secure the tray trial 12 to the proximal end 18 of the patient's tibia 20.

Figure 4:
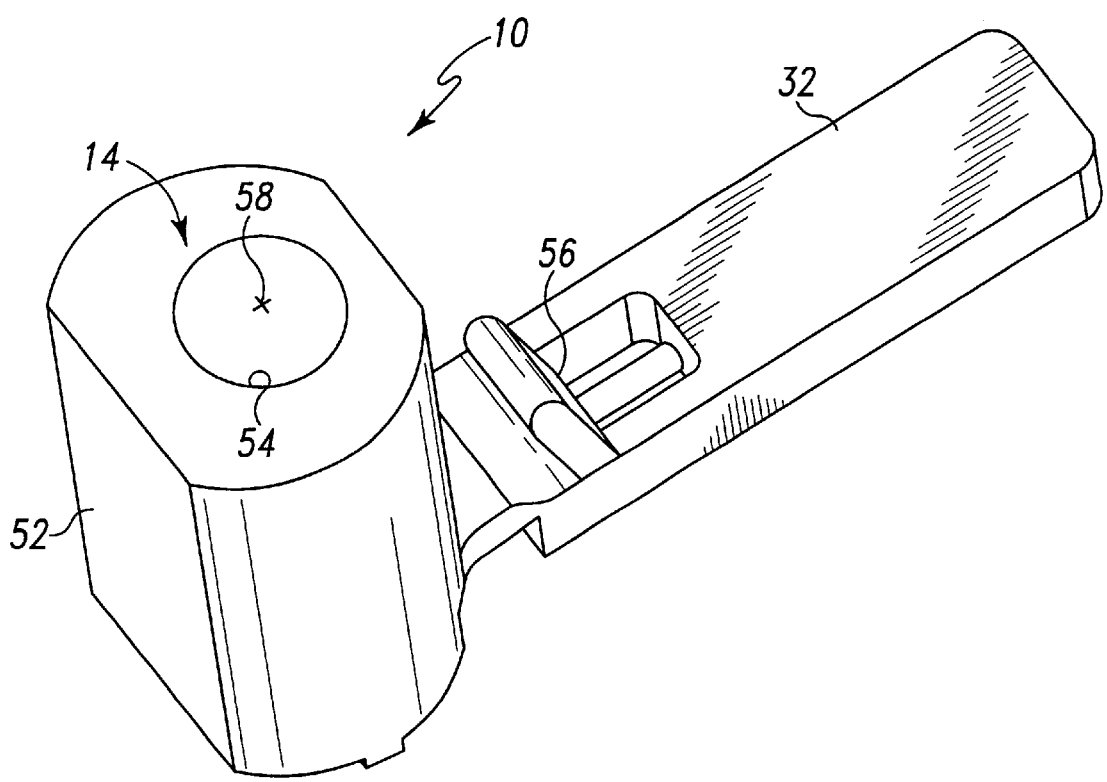
FIG. 4 is a top perspective view of a drill guide which incorporates the features of the present invention therein.
Figure 5:
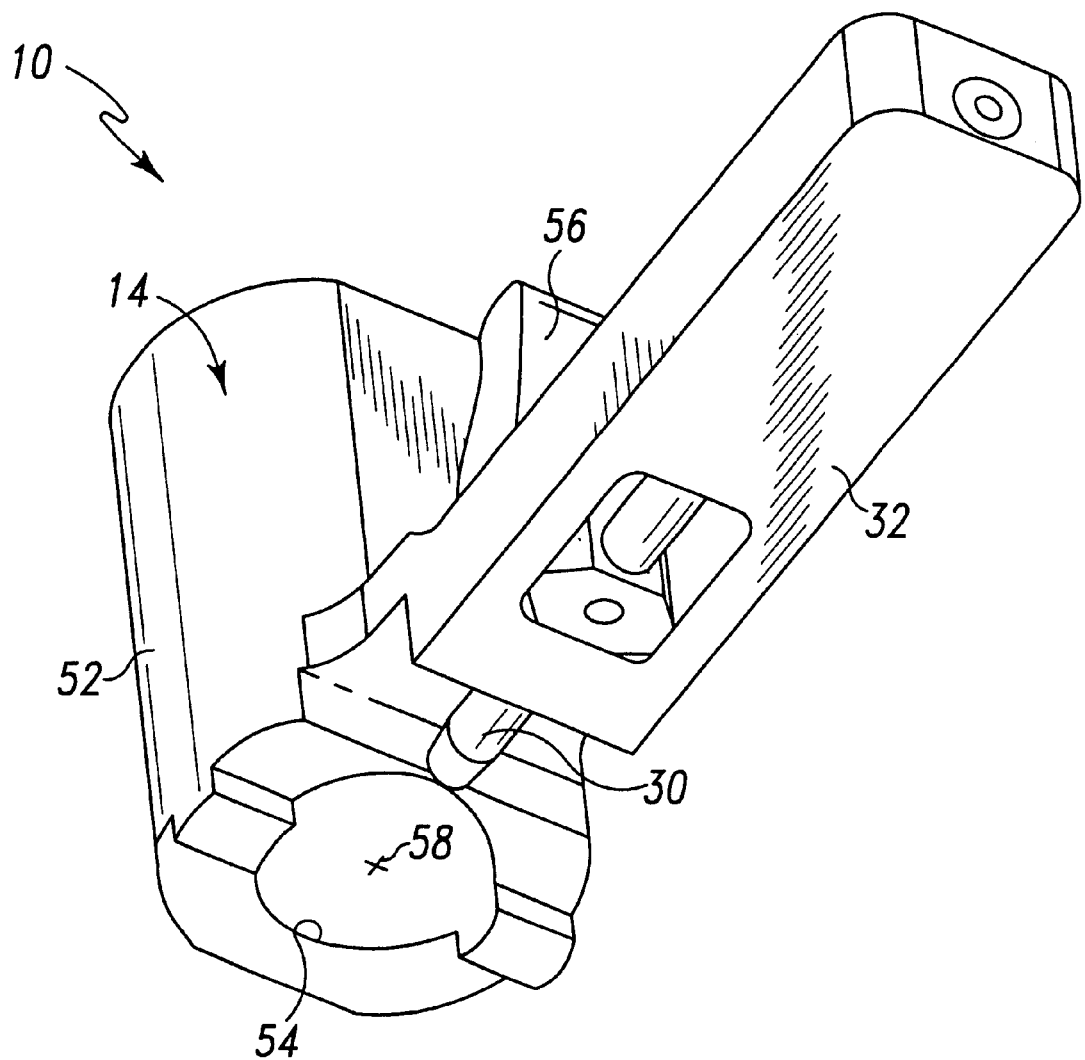
FIG. 5 is a bottom perspective view of the drill guide of FIG. 4.

As shown in FIGS. 4–6, the drill guide 14 has a guide body 52 having an elongated bore 54 extending therethrough. Moreover, as alluded to above, the drill guide 14 also includes a handle assembly 32. The handle assembly 32 includes a spring loaded lever 56 which is operatively coupled to the locking pin 30. In particular, when the lever 56 is pulled, moved, or otherwise urged, the locking pin 30 is retracted into the body of the handle assembly 32 thereby allowing the locking pin 30 to be removed from the pin receiving aperture 28 of the rim 26 of the tray trial 12. However, once locking pin 30 is aligned with the pin receiving aperture 28 and the lever 56 is released, the spring (not shown) associated with the locking pin 30 urges the locking pin 30 outwardly so as to lock or otherwise engage the locking pin 30 in the pin receiving aperture 28 of the rim 26 of the tray trial 12.

When secured to the tray trial 12, the elongated bore 54 of the drill guide 14 is aligned with the plate opening 36 of the tray trial 12. In particular, the elongated bore 54 of the drill guide 14 has a center point 58. When the drill guide 14 is attached to the tray trial 12, the center point 58 of the elongated bore 54 is substantially coaxial with the center point 50 of the plate opening 36 of the tray trial 12. As shall be discussed below in greater detail, the such a configuration of the drill guide 14 allows for the aligning and drilling of a first drilled hole in the patient's tibia 20.

As shown in FIGS. 7–9, the drill/broach guide 16 has a guide body 60 having guide opening 62 defined therein. As with the drill guide 14, the drill/broach guide 16 also includes a handle assembly 32 having a spring loaded lever 56 which is operatively coupled to the locking pin 30. The lever 56 may be operated in a similar manner to as described above in regard to the drill guide 14 in order to allow for selective attachment and detachment of the drill/broach guide 16 to/from the rim 26 of the tray trial 12.

Figure 10:
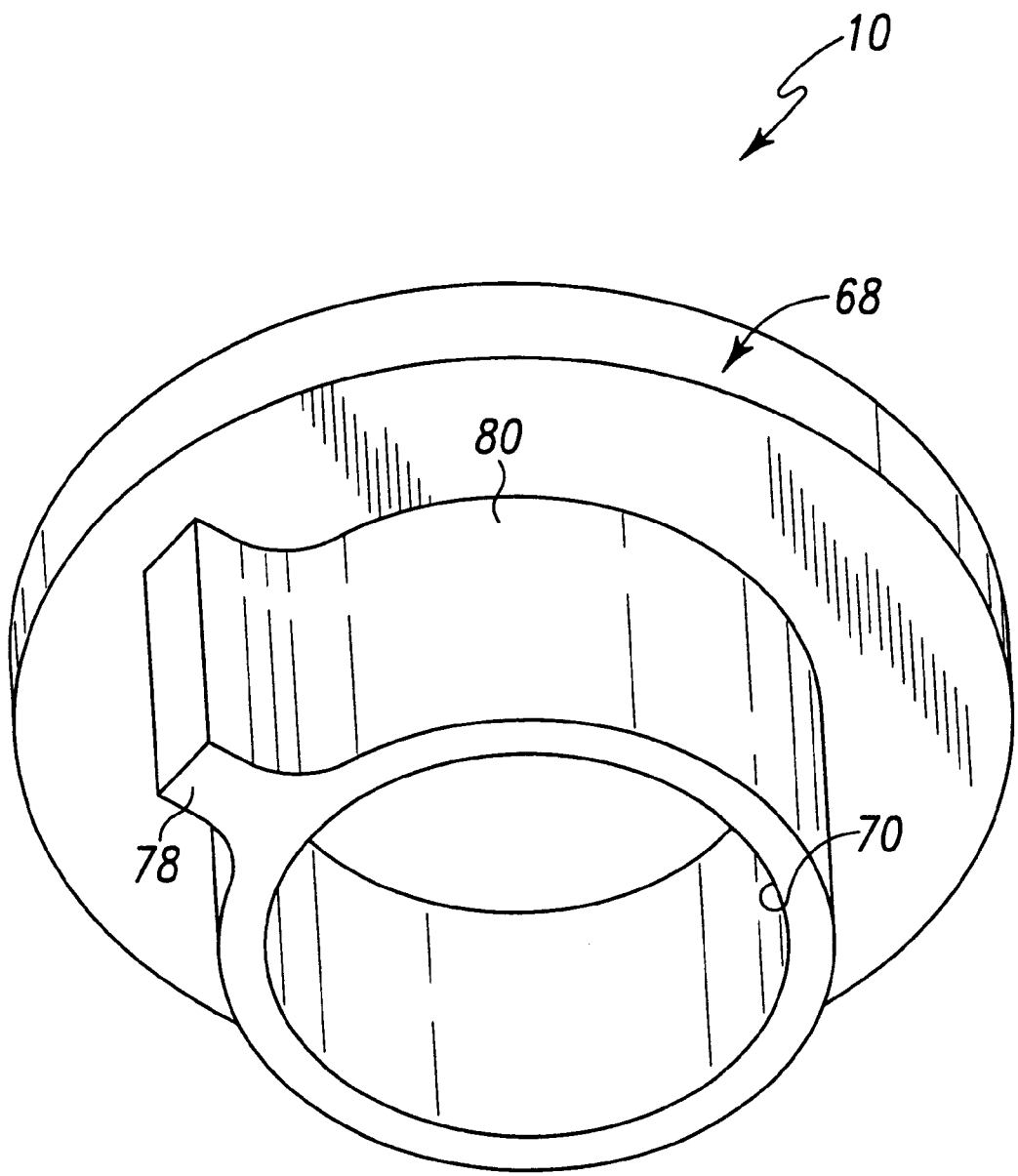
FIG. 10 is a perspective view of a drill bushing that is securable to the drill/broach guide of FIG. 7.
Figure 11:
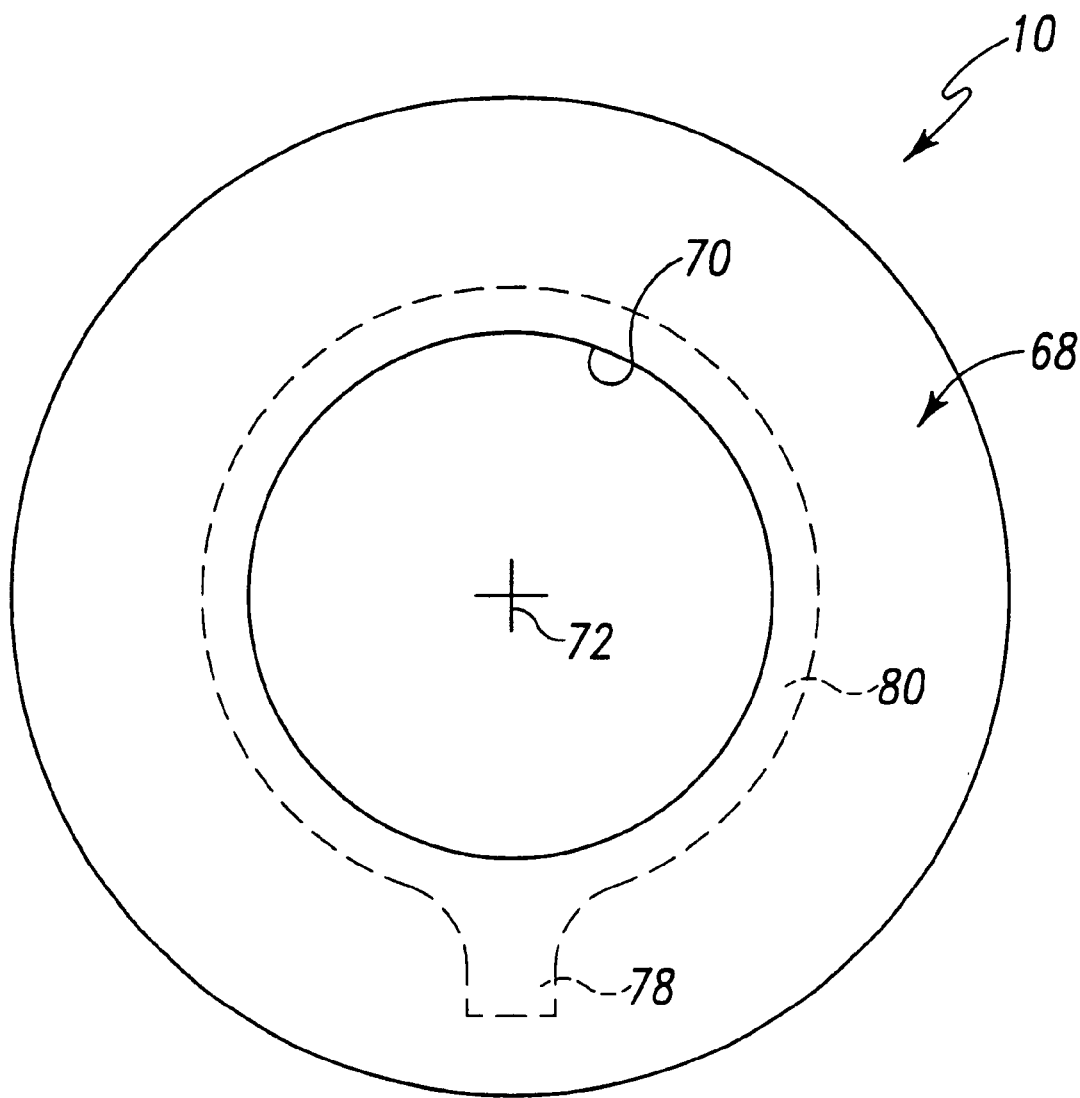
FIG. 11 is a top elevational view of the drill bushing of FIG. 10.
Figure 12:
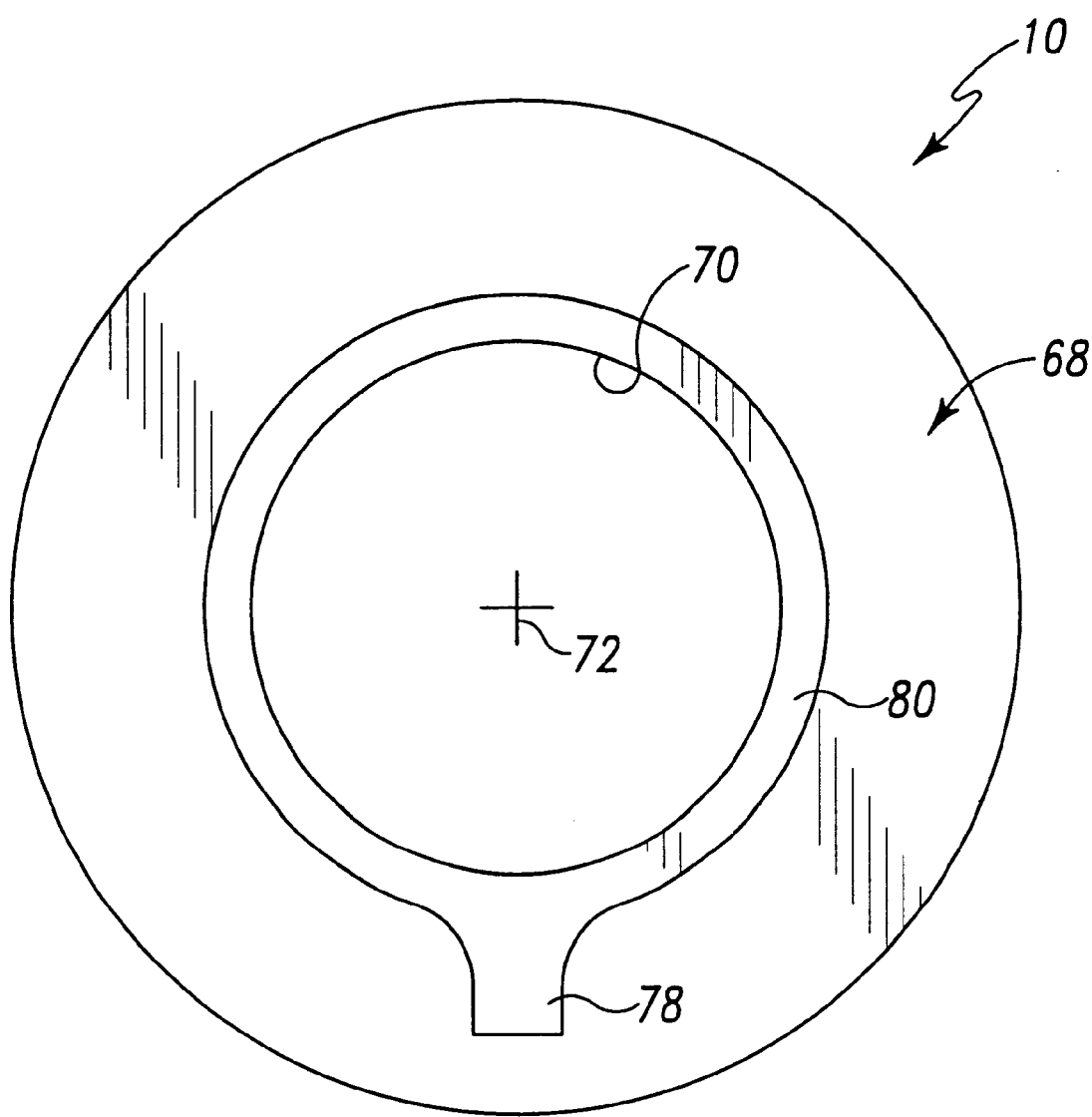
FIG. 12 is a bottom elevational view of the drill bushing of FIG. 10.

As shown in FIGS. 8 and 9, the guide opening 62 includes two distinct bushing-receiving portions 64, 66. As their name implies, the bushing-receiving portions 64, 66 of the guide opening 62 are configured to receive a drill bushing 68 (see FIGS. 10–12). The drill bushing 68 is positionable in either the bushing-receiving portion 64 or the bushing-receiving portion 66 in order to facilitate drilling of a hole in the proximal end 18 of the tibia 20 in either one of two offset directions. In particular, as shown in FIG. 10, the drill bushing 68 has a bore 70 extending therethrough. The bore 70 has a center point 72 (see FIGS. 11 and 12) which, when the drill bushing 68 is assembled with the drill/broach guide 16 and secured to the tray trial 12, is offset from the center point 50 of the plate opening 36 of the tray trial 12 when the drill bushing 68 is positioned in either one of the bushing-receiving portions 64, 66. Specifically, if the drill bushing 68 is positioned in the bushing-receiving portion 64 while the drill/broach guide 16 is secured to the tray trial 12, the center point 72 of the bore 70 is offset in a first direction from the center point 50 of the plate opening 36 (see FIG. 19). However, if the drill bushing 68 is positioned in the bushing-receiving portion 66 while the drill/broach guide 16 is secured to the tray trial 12, the center point 72 of the bore 70 is offset in a second direction from the center point 50 of the plate opening 36.

What is meant herein by the term "offset" is that two or more structures, features, or reference points are arranged in a non-coaxial relationship with one another. For example, two center points are "offset" from one another if the center points are not arranged in a coaxial relationship with one another. Similarly, a first drilled hole is offset from a second drilled hole if the two drilled holes are not coaxially arranged with one another.

Referring again to FIGS. 7–9, the guide opening 62 of the drill/broach guide 16 also has a pair of keying portions 74, 76 defined therein. The keying portions 74, 76 are provided to prevent rotational movement of the drill bushing 68 when it is positioned in the bushing-receiving portions 64, 66, respectively, of the guide opening 62. In particular, the drill bushing 68 has a keying tab 78 extending outwardly from a sidewall 80 thereof (see FIG. 10). The keying tab 78 is positioned in the keying portion 74 of the guide opening 62 when the drill bushing 68 is positioned in the bushing-receiving portion 64. Conversely, when the drill bushing 68 is positioned in the bushing-receiving portion 66, the keying tab 78 is positioned in the keying portion 76 of the guide opening 62.

As shown in FIG. 8, the guide body 60 of the drill/broach guide 16 includes a blocking protrusion 94. The blocking protrusion 94 extends inwardly into the guide opening 62 at a location which divides or otherwise separates the guide opening 62 into the two distinct bushing-receiving portions 64, 66. In such a manner, the blocking protrusion 94 ensures that the drill bushing 68 is fully seated in either the first or second bushing-receiving portions 64, 66 when the drill bushing 68 is inserted into the guide opening 62. Indeed, the configuration of the blocking protrusion 94, together with the configuration of the keying portions 74, 76, prevents the drill bushing 68 from being located at any location within the guide opening 62 other than the designated locations within the first or second bushing-receiving portions 64, 66. As such, the configuration of the blocking protrusion 94 prevents sliding movement of the drill bushing 68 between the bushing-receiving portions 64, 66 thereby requiring that the drill bushing 68 be removed from the guide opening 62 and thereafter replaced therein if the position of the drill bushing 68 is to be changed from one bushing-receiving portion 64, 66 of the guide opening 62 to the other.

As shown in FIG. 8, the guide opening 62 also includes a blade-receiving portion 82. The blade-receiving portion 82 is provided to allow a cutting assembly or punch 84 associated with a broach assembly 86 to be advanced through the guide opening 62 (see FIG. 22). In particular, the punch 84 includes a number of cutting blades 88, 90, 92. The punch 84 is configured such that during advancement of the punch through the guide opening 62 of the drill/broach guide 16, (1) the cutting blade 88 is advanced through the keying portion 74, (2) the cutting blade 90 is advanced through the blade-receiving portion 82, and (3) the cutting blade 92 is advanced through the keying portion 76. In such a manner, the keying portions 74, 76 also function as "blade-receiving" portions.

Figure 13:
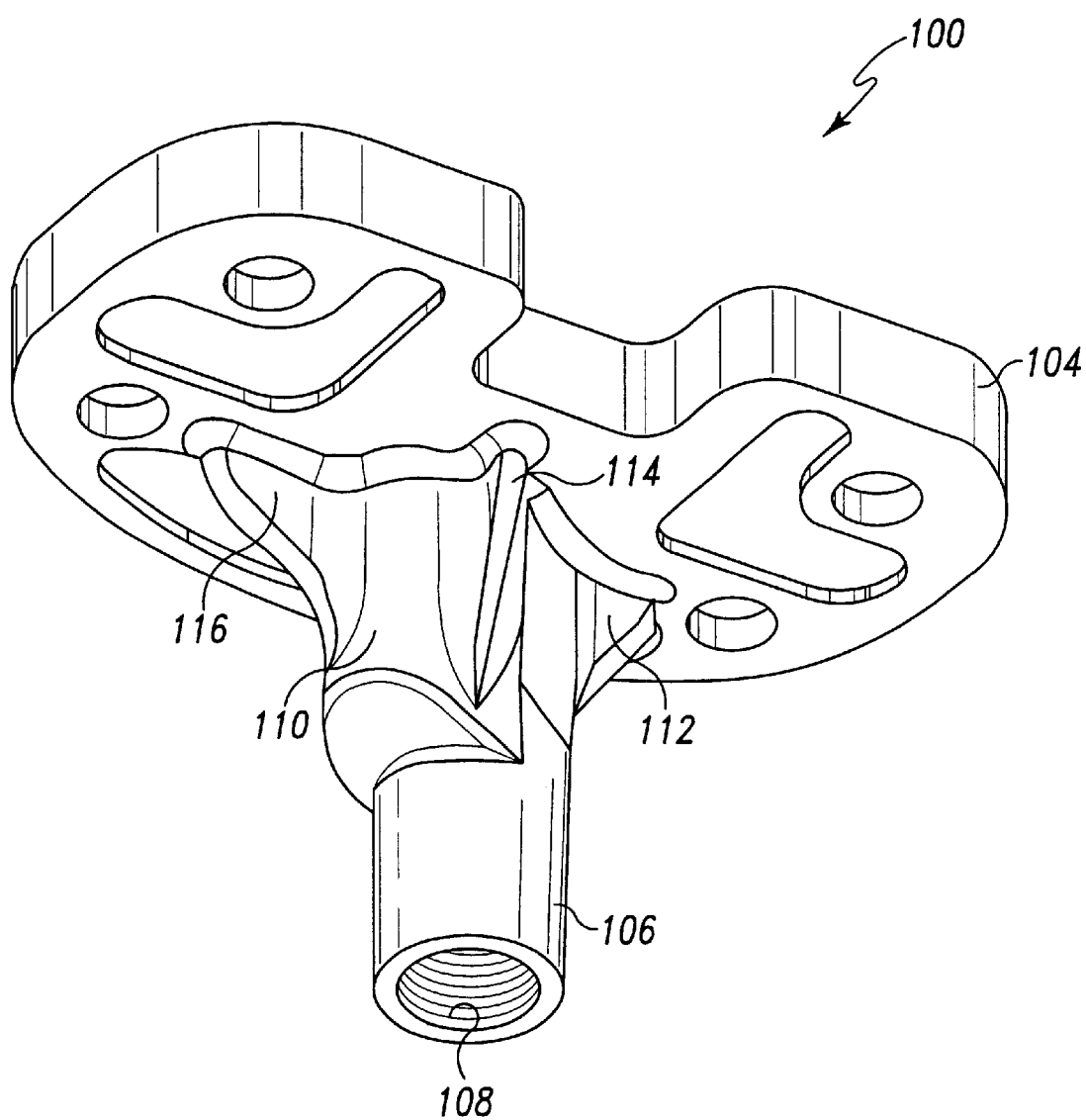
FIGS. 13 and 14 are perspective views of a tibial implant component which may be implanted by use of the surgical instrument assembly of the present invention.
Figure 14:
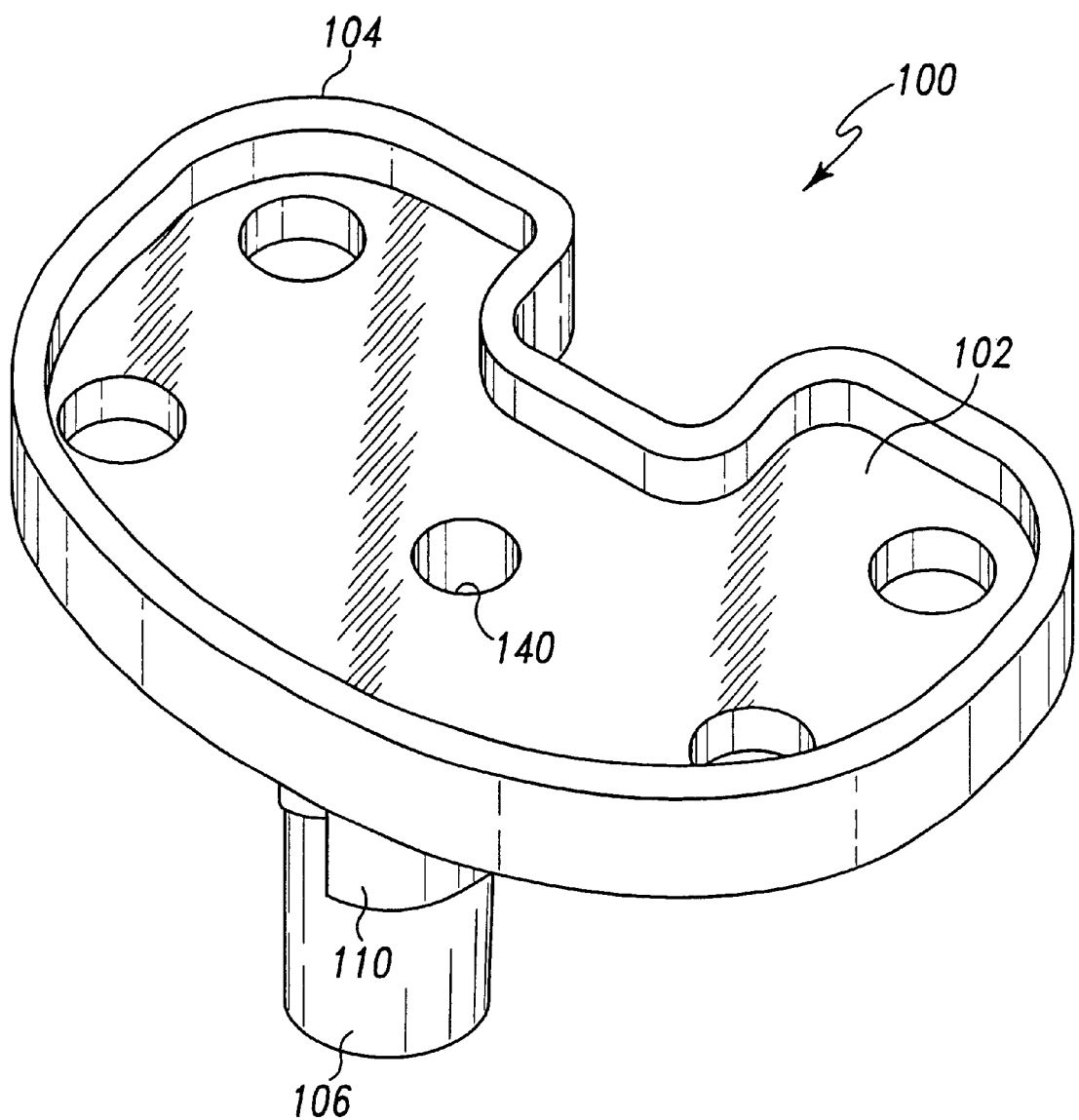
Figure 15:
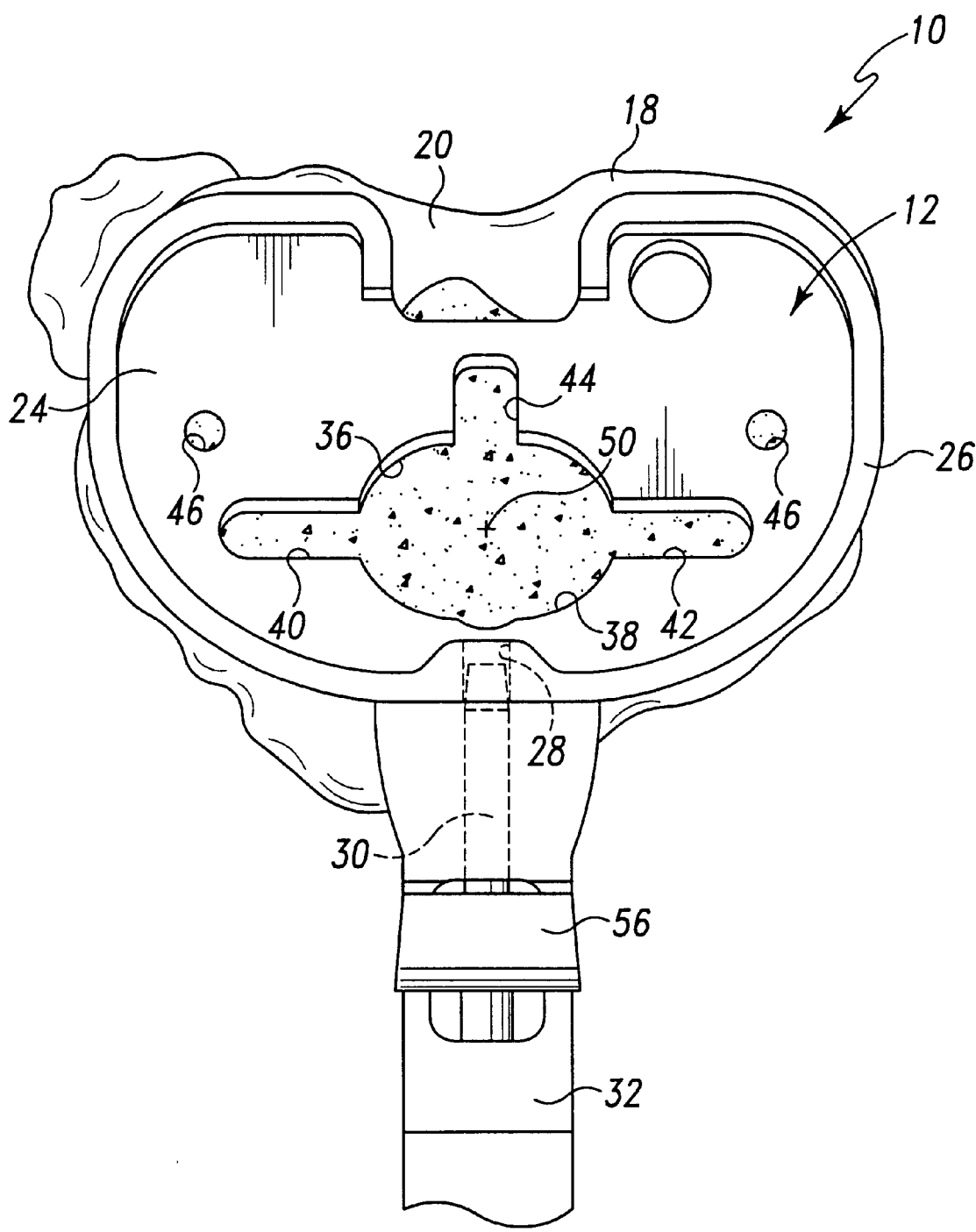
FIGS. 15–22 show a patient's tibia during various steps of a procedure for surgically preparing the proximal end thereof for implantation of the tibial implant component of FIGS. 13 and 14.

Referring now to FIGS. 13 and 14, there is shown a tibial implant 100 which may be implanted into the patient's tibia 20 by use of the surgical instrument assembly 10 of the present invention. The implant 100 includes a plate 102 which has a rim 104 extending around the periphery thereof. An implantable bearing insert (not shown) similar to a trial bearing insert 118 (see FIG. 16) is securable to the plate 102 of the implant 100 in order to provide a surface on which a distal end portion of a femoral component 120 (see FIG. 16) may bear. The tibial implant also includes a downwardly extending stem 106. The stem 106 is adapted to be implanted into the previously drilled medullary canal of the patient's tibia 20. The stem 106 has a threaded aperture 108 on the distal end thereof. An elongated stem extension (not shown) may be threadingly secured to the distal end of the stem 106 in order to increase the length of the stem 106. Alternatively, a plastic cap (not shown) constructed of implantable material may be utilized to cap the distal end of the stem 106 by advancing a threaded post (not shown) associated with the cap into the threaded aperture 108.

The tibial implant 100 is preferably embodied as an offset tibial implant. In particular, as shown in FIG. 14, a threaded bore 140 extends downwardly into a generally cylindrically-shaped sub-stem member 110. The center line of the threaded bore 140 is coaxial with the center of the plate 102. The threaded bore 140 is provided to threadingly receive a threaded (or smooth) post associated with the implantable bearing insert (not shown) so as to secure the insert to the tibial implant 100. The center line of the stem 106 is offset from the center line of the threaded bore 140. As described above, such an offset allows the plate 102 to be centered on the proximal end 18 of the tibia 20, while also allowing the stem 106 to extend into the medullary canal of a patient's tibia 20 in the event that the medullary canal is not "centered" in the tibia 20. It should be appreciated that the stem 106 may be offset from the center of the plate 102 in the direction shown in FIG. 13, or, alternatively, in any other direction which is needed to accommodate the anatomy of a given patient's tibia 20.

As shown in FIG. 13, the tibial implant 100 also includes a number of triangular-shaped fins 112, 114, 116. The fins 112, 114, 116 form a generally T-shaped configuration with the fin 112 extending out of the stem 106 and the fins 114, 116 extending out of the sub-stem member 110. The fins 112, 114, 116 are provided to prevent rotation of the tibial implant 100 subsequent to implant thereof.

OPERATION OF THE PRESENT INVENTION

In operation, the surgical instrument assembly 10 of the present invention is utilized to surgically prepare a patient's tibia 20 for implantation of a tibial component such as the tibial component 100 during performance of a knee replacement procedure. In order to do so, as shown in FIGS. 15–22, the proximal end portion of the patient's tibia 20 is first resected by use of, for example, a bone saw (not shown). Thereafter, with the knee in maximal flexion, the patient's tibia 20 is subluxed anteriorly with a tibia retractor (not shown). A tray trial 12, having a handle assembly 32 secured thereto, is then selected, as shown in FIG. 15. In particular, a group of tray trials 12 may be provided which includes tray trials configured in a number of different sizes. Hence, a tray trial 12 which provides the greatest coverage of the resected surface of the tibia 20 without overhanging anteriorly of the midcoronal plane of the tibia 20 is selected from such a group.

Figure 16:
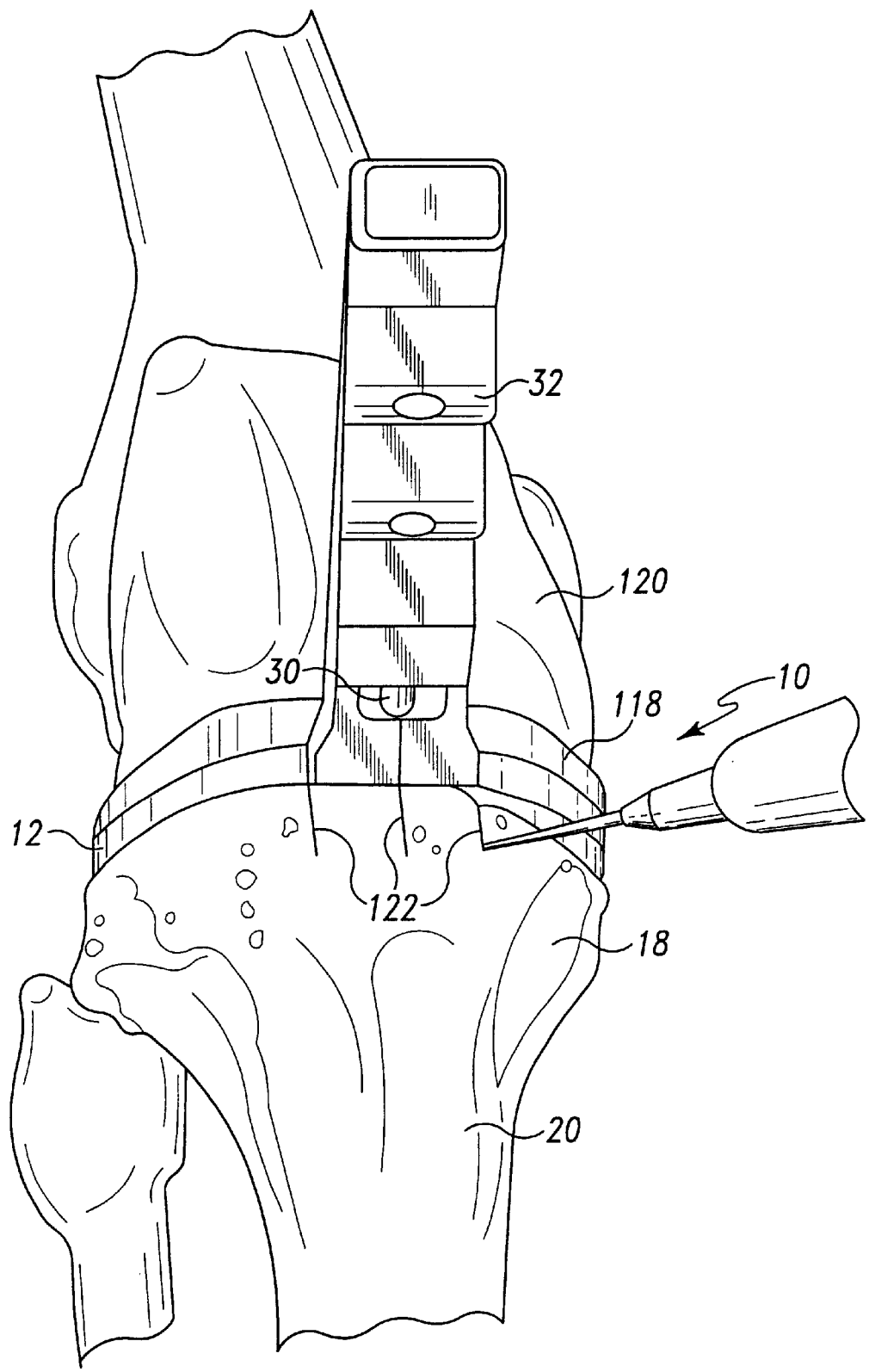

As shown in FIG. 16, a number of the trial prostheses associated with the knee replacement procedure are then assembled and held in place. For example, the bearing insert 118 and the femoral component 120 are positioned in their respective positions relative to the tray trial 12. Once the prostheses are in place, the knee is extended in order to allow the surgeon to assess the medial and lateral stability of the knee along with the overall alignment of the knee in both the anterior/posterior and medial/lateral planes. If the surgeon encounters any potential instability, a larger bearing insert 118 may be substituted for the current bearing insert 118 in order to increase stability in flexion and extension along with allowing for full extension.

Moreover, during such a "mock up", the surgeon may adjust the rotational alignment of the tray trial 12 while the knee is positioned in full extension. The handle assembly 32 is utilized to rotate the tray trial 12 and the bearing insert 118 relative to the femoral component 120. Once each of the components associated with the prostheses is positioned in a desired location, the location of the tray trial 12 is marked so as to be recreated at a later time. In particular, as shown in FIG. 16, electrocautery is utilized to create a number of alignment marks 122 on the anterior tibial cortex of the patient's tibia 20. Such marks 122 correspond with features on the tray trial 12 and/or the handle assembly 32 thereby allowing the current orientation of the tray trial 12 to be reproduced by subsequent realignment of the tray trial 12 relative to the marks 122. Once the alignment marks 122 have been formed in the tibia 20, the trial prostheses may be disassembled or otherwise removed from the knee.

Figure 17:
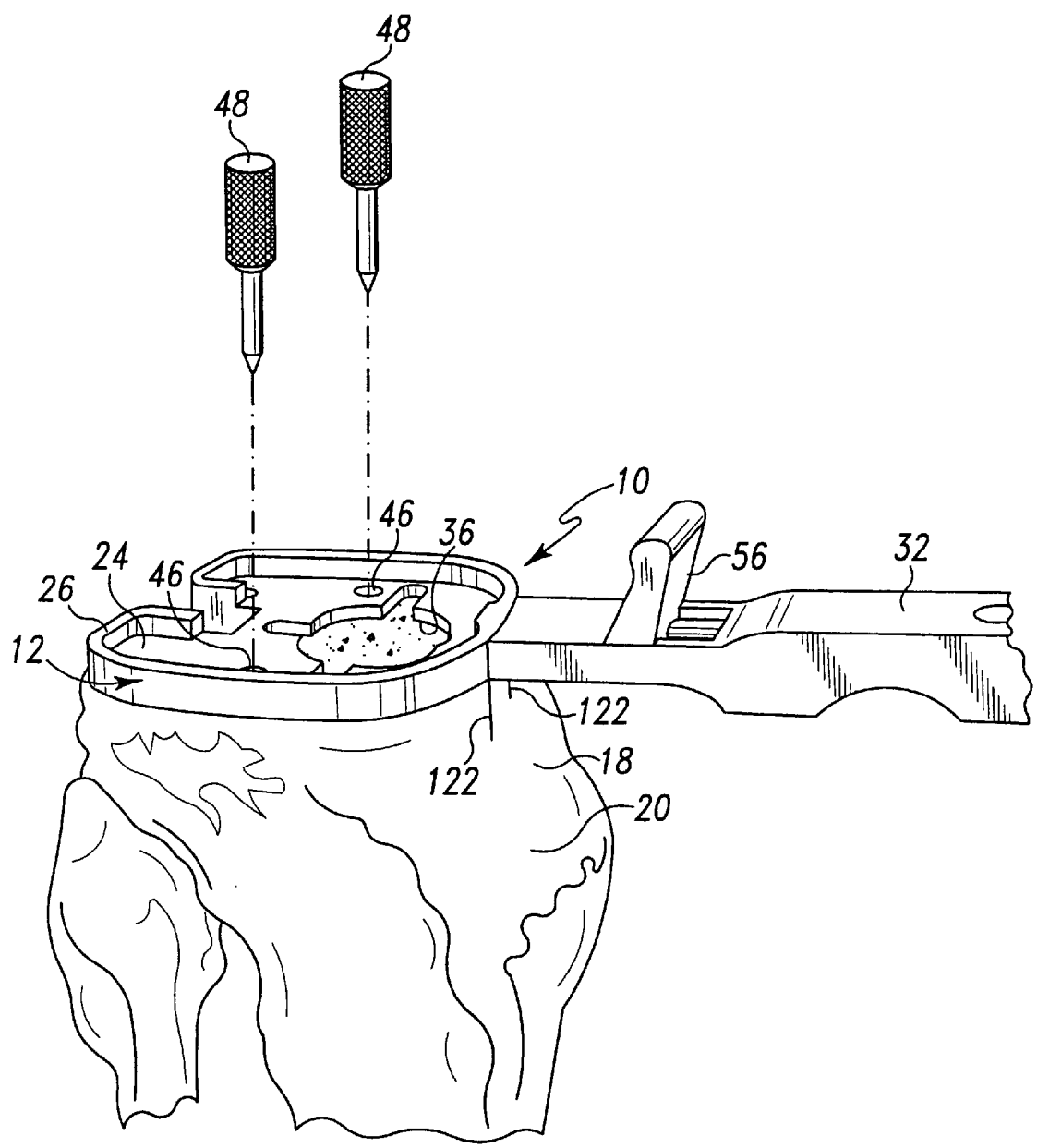

Thereafter, as shown in FIG. 17, with the knee in substantially full flexion and the tibia subluxed anteriorly, the tray trial 12 is positioned in the desired rotational position by use of the alignment marks 122. Once aligned, the tray trial 12 is secured to the resected surface of the tibia 20 by use of the fixation pins 48 (or screws, not shown) which are inserted through the fastener openings 46 defined in the plate 24 of the tray trial 12. It should be appreciated that a pair of holes (not shown) may be drilled in the tibia 20 to receive the fixation pins 48 prior to insertion thereof.

Figure 18:
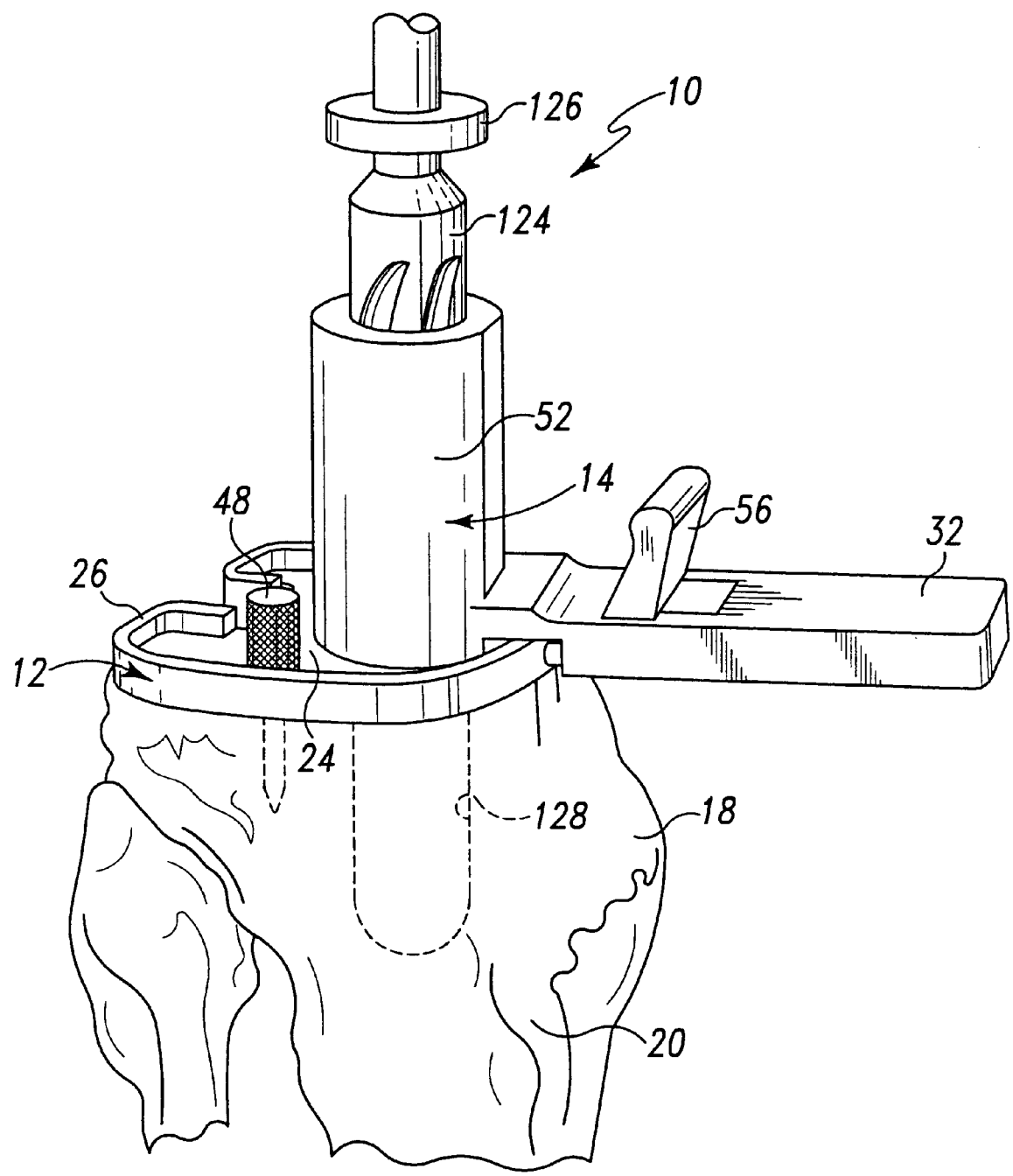

As shown in FIG. 18, the handle assembly 32 which was utilized to align the tray trial 12 is then removed so that the handle assembly 32 associated with the drill guide 14 may be secured to the rim 26 of the tray trial 12 by advancing the locking pin 30 of the handle 32 into the pin receiving aperture 28. Once the drill guide 14 has been secured to the tray trial 12, a bone drill 124 is advanced through the elongated bore 54 of the drill guide 14 in order to drill a drilled hole 128 in the patient's tibia 20. As shown in FIG. 18, the bone drill 124 may be equipped with a depth stop 126 which engages the body 52 of the drill guide 14 once the bone drill 124 has drilled to a desired depth in the patient's tibia 20. It should be appreciated that the drilled hole 128 is provided to receive the sub-stem member 110 of the tibial component 100. As such, it should further be appreciated that the drilled hole 128 is centered or otherwise aligned with the both the center of the plate 24 of the tray trial 12 (i.e. the center point 50 of the plate opening 36) and the center of the tibia 20.

The next step in the procedure is to drill an offset hole in the tibia to receive the stem 106 of the tibial implant 100. However, in order to do so, the surgeon must determine the direction in which to offset such a drilled hole. Specifically, the surgeon must determine in which direction the medullary canal of the patient's tibia 20 is offset from the center of the bone. Such a determination is often made through the use of roentgenographic evaluation. Alternatively, the direction of offset may be assessed intraoperatively.

Figure 19:
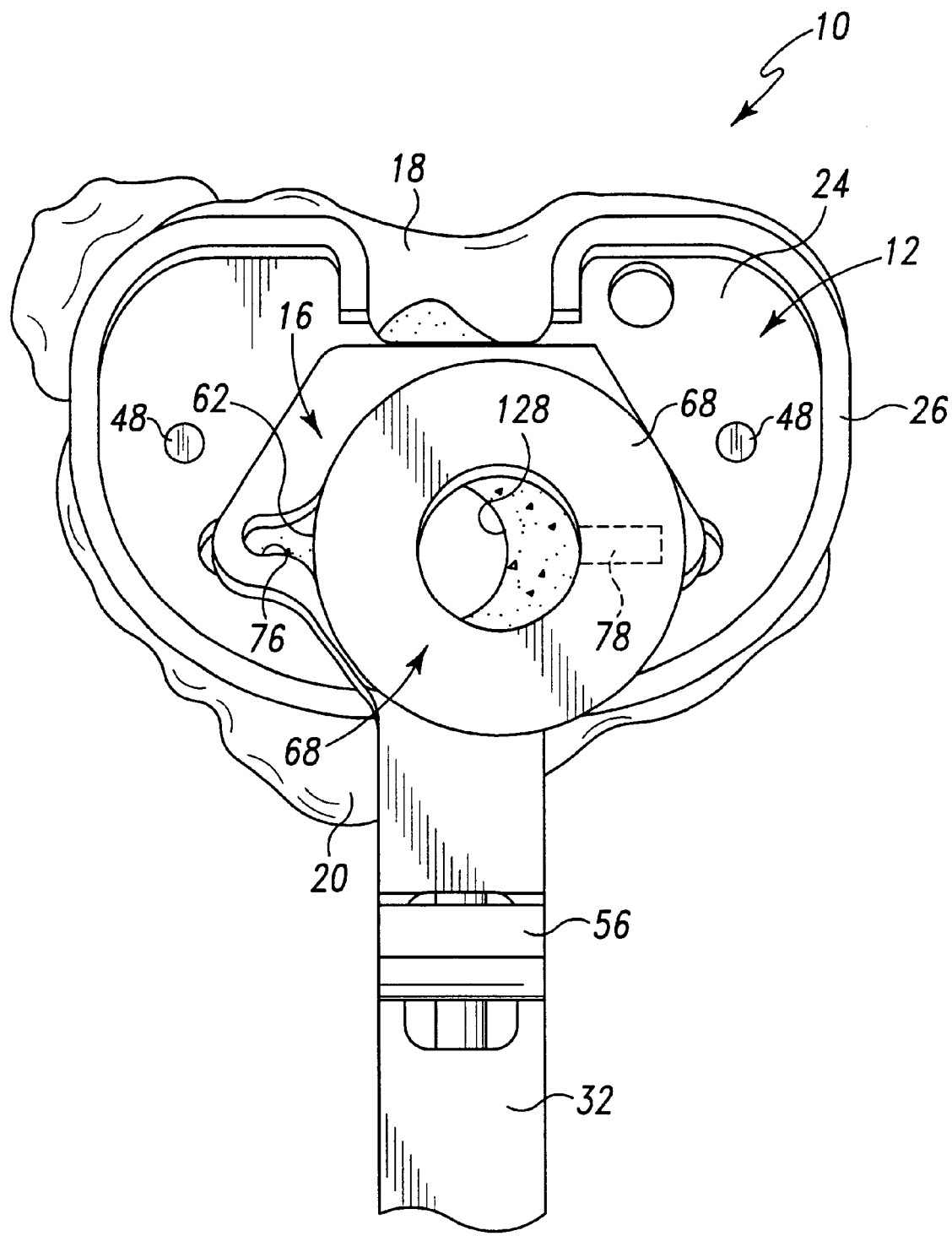

In any event, once the direction of the necessary offset has been determined, a properly sized drill/broach guide 16 is then selected, as shown in FIG. 19. In particular, a group of drill/broach guides 16 may be provided which includes drill/broach guides which are configured in a number of different sizes. This allows for the formation of offset holes of varying diameters along with varying distances from the center of the patient's tibia 20. Hence, a drill/broach guide 16 which provides for the formation of a hole which is of the desired diameter and offset the desired distance from the center of the proximal tibia 18 is selected from such a group. The selected drill/broach guide 16 is then secured to the tray trial 12 by use of its handle assembly 32.

Thereafter, the drill bushing 68 is inserted into one of the bushing-receiving portions 64, 66 of the guide opening 62. In particular, the drill bushing 68 is inserted into the bushing-receiving portion 64 if the surgeon has decided to drill a hole which is offset from the drilled hole 128 in a first direction. Conversely, the drill bushing 68 is inserted into the bushing-receiving portion 66 if the surgeon has decided to drill a hole which is offset from the drilled hole 128 in a second direction. It should be appreciated that during such insertion of the drill bushing 68 into the guide opening 62, the keying tab 78 associated with the bushing 68 is advanced into the respective keying portions 74, 76 of the guide opening 62.

Figure 20:
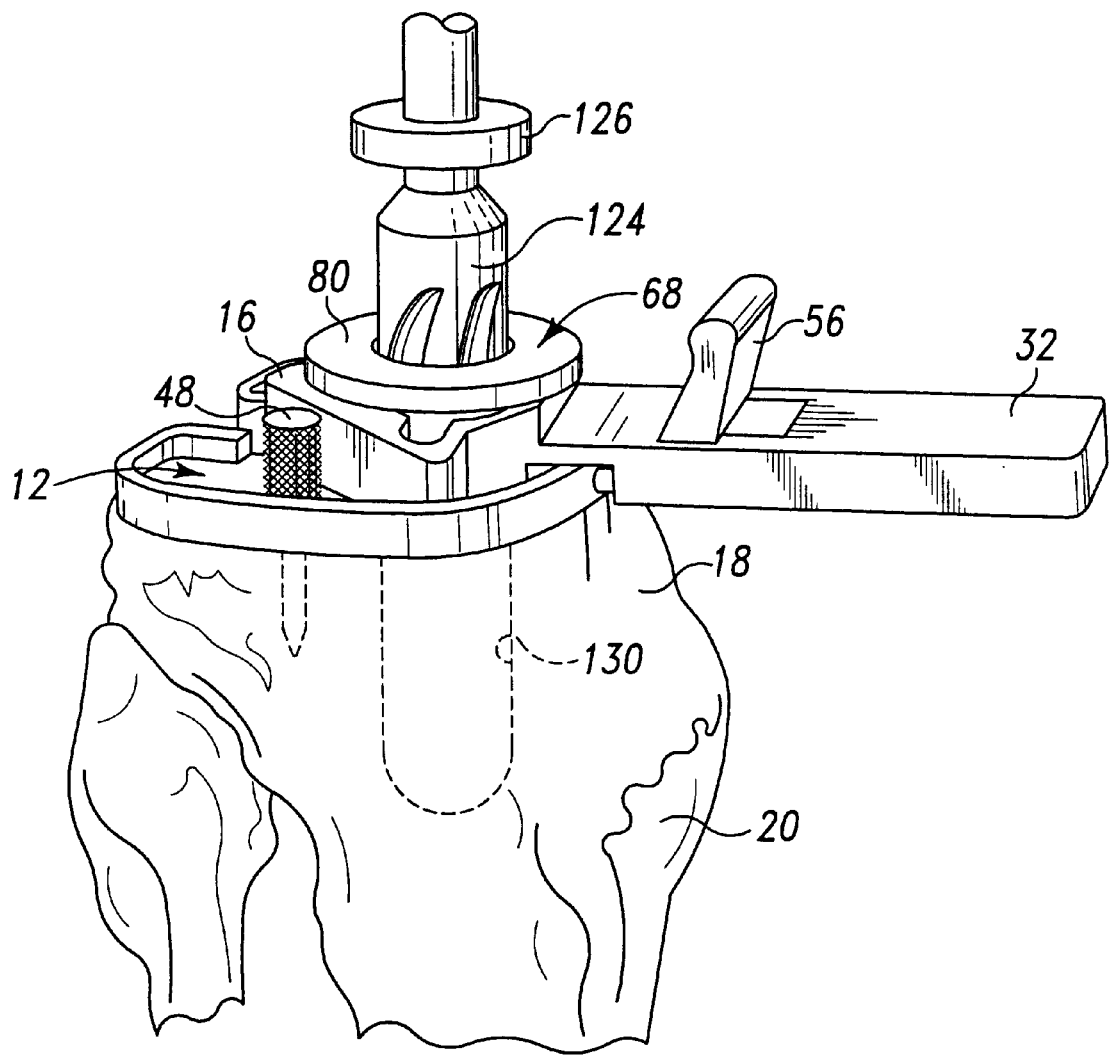

As shown in FIG. 20, once the drill bushing 68 has been installed, the bone drill 124 is advanced through the bushing bore 70 of the drill bushing 68 in order to drill a drilled hole 130 in the patient's tibia. As described above, the bone drill 124 may be equipped with a depth stop 126 which engages the body 80 of the drill bushing 68 once the bone drill 124 has drilled to a desired depth in the patient's tibia 20. Moreover, it should be appreciated that the holes drilled by the bone drill 124 (i.e. the holes 128, 130) may possess the same or varying diameters based on the configuration of the tibial implant 100 that is to be implanted. It should also be appreciated that the drilled hole 130 receives the stem 106 of the tibial component 100 during subsequent implantation thereof. As such, it should be apparent from the above description that the drilled hole 130 is offset from the drilled hole 128 (and hence offset from both the center of the plate 24 of the tray trial 12 and the center of the proximal tibia 18).

Figure 21:
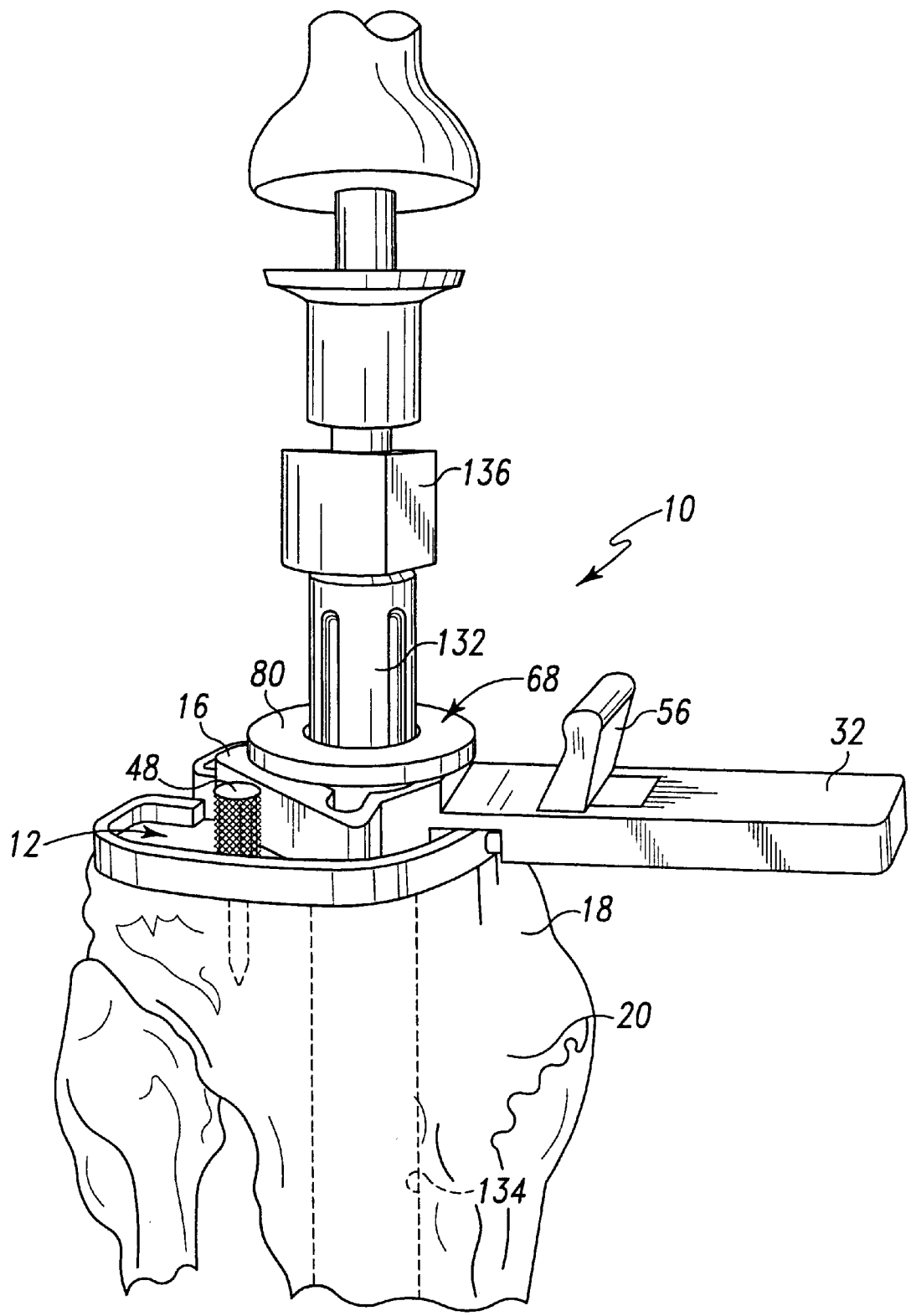

As shown in FIG. 21, if an extension stem (not shown) is to be attached to the stem 106 prior to the implantation of the tibial component 100, a stem punch or broach 132 is advanced through the bushing bore 70 of the drill bushing 68 in order to form a punched hole 134 in the patient's tibia 20. Since the stem punch 132 is advanced through the same guide as the bone drill 124 (i.e. the drill bushing 68), the punched hole 134 is coaxially arranged with the drilled hole 130 thereby effectively deepening the depth of the drilled hole 130 so as to allow for the use of an extension stem. Similarly to the bone drill 124, the stem punch 132 may be equipped with a depth stop 136 which engages the body 80 of the drill bushing 68 once the stem punch 132 has punched (i.e. broached) to a desired depth in the patient's tibia 20. It should be appreciated that if a stem extension is not to be secured to the stem 106 of the tibial implant 100, the step of forming the punched hole 134 with the stem punch 132 is not performed.

Figure 22:
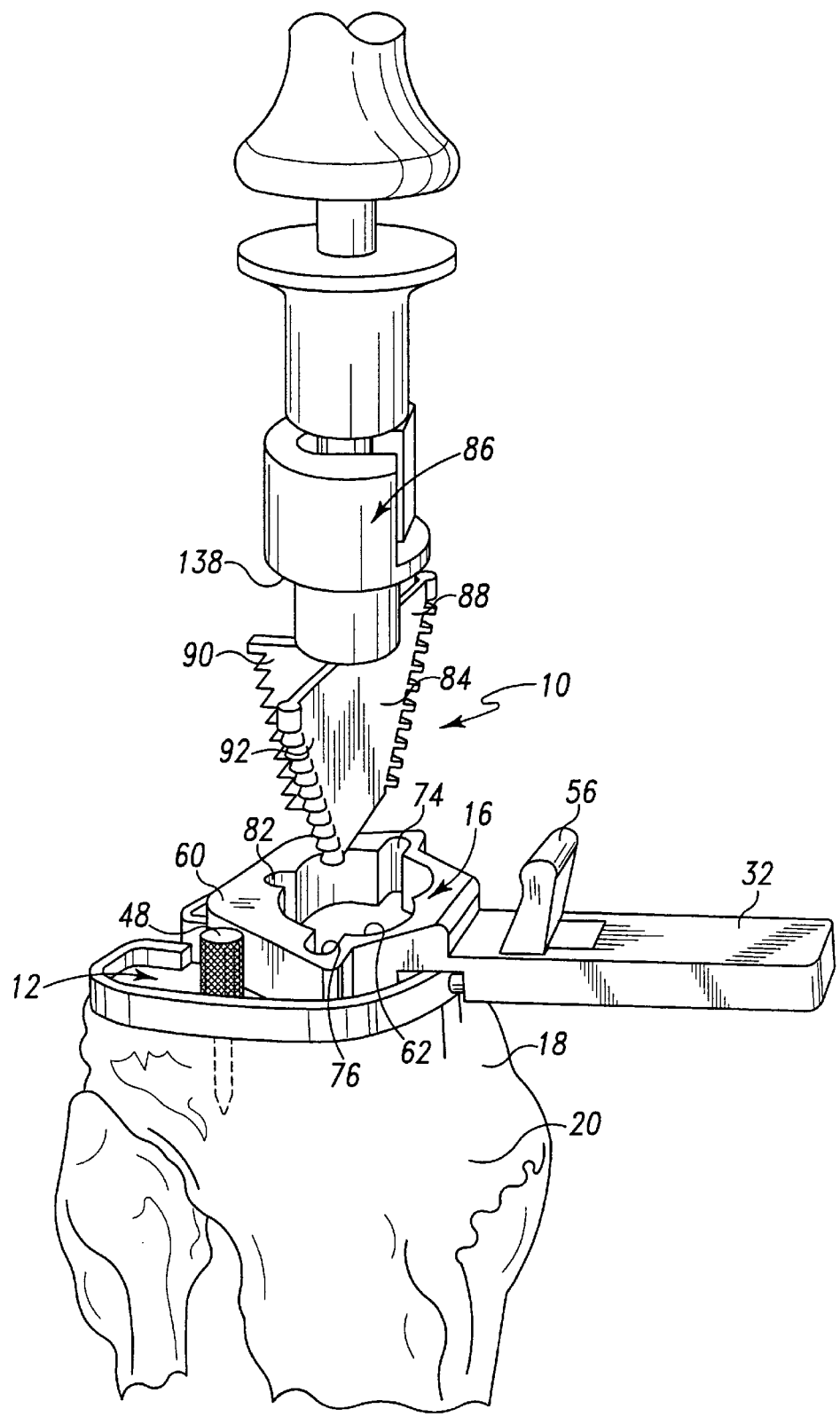

As shown in FIG. 22, the drill bushing 68 is then detached from the drill/broach guide 16 in order to allow for use of the broach assembly 86. In particular, the cutting assembly or punch 84 associated with a broach assembly 86 is then advanced through the guide opening 62 in order to punch, broach, or otherwise form a number of punched holes in the tibia 20 with the cutting blades 88, 90, 92. The punch 84 is configured such that during such advancement of the punch through the guide opening 62 of the drill/broach guide 16, (1) the cutting blade 88 is advanced through the keying portion 74, (2) the cutting blade 90 is advanced through the blade-receiving portion 82, and (3) the cutting blade 92 is advanced through the keying portion 76. It should be appreciated that the holes formed by the punch 84 are provided to receive the fins 112, 114, 116 of the tibial component 100. It should be appreciated that the broach assembly 86 may be equipped with a depth stop 138 which engages the guide body 60 of the drill/broach guide 16 once the punch 84 has been advanced to a desired depth in the patient's tibia 20.

Once broached or punched in such a manner, the trial assembly may be disassembled. In particular, the drill/broach guide 16 is first detached from the rim 26 of the tray trial 12 by retracting the lever 56 so as to allow the locking pin 30 to be retracted from the pin-receiving aperture 28 of the rim 26. Thereafter, the drill/broach guide 16 is lifted away from the tray trial 12. The fixation pins 48 may then be removed so as to allow the tray trial 12 to be detached from the proximal tibia 18.

Figure 23:
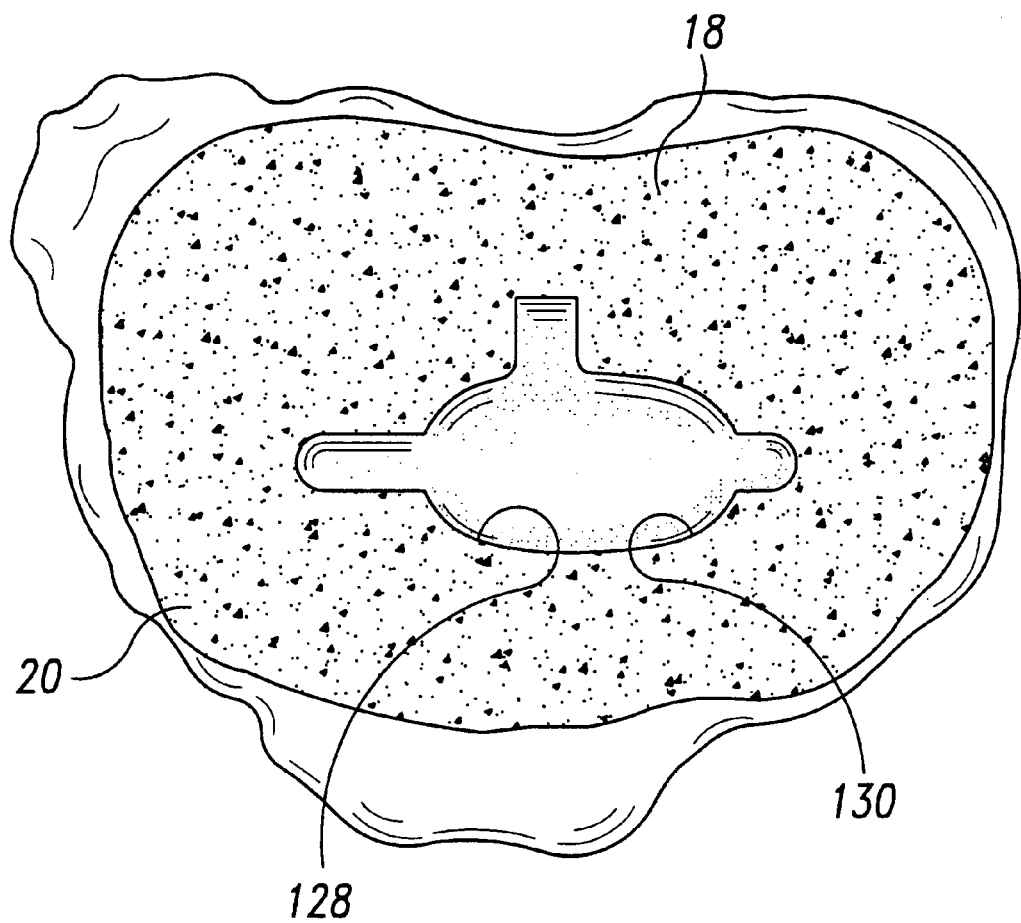
FIG. 23 shows the proximal end of the patient's tibia subsequent to performance of the steps shown in FIGS. 15–22.

As shown in FIG. 23, the resultant features formed in the proximal end 18 of the patient's tibia 20 are configured to receive the tibial implant 100. In particular, the collective opening defined by the drilled holes 130, 128 provide an opening into which the stem 106 and the sub-stem member 110 may be inserted, respectively. Moreover, the fins 112, 114, 116 may be inserted into the holes formed by the blades 88, 90, 92 of the punch 84 so as to prevent rotation of the tibial component 100 relative to the patient's tibia 20 subsequent to implantation thereof. It should be appreciated that the tibial implant 100 may be press fit into the tibia 20, or, alternatively, may be secured to the tibia 20 by use of bone cement.

Hence, as described herein, the surgical instrument assembly 10 of the present invention provides numerous advantages over heretofore designed instrument assemblies. For example, the modular design of the surgical instrument assembly 10 of the present invention allow for the surgical preparation of a tibia for implantation of an offset tibial component without the need to stock or otherwise maintain large numbers of separate instruments. Moreover, the configuration of the guide opening 62 of the drill/broach guide 16 allows for relatively quick and precise positioning of the drill bushing 68 and hence the bone drill 124.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the surgical instrument assembly and associated method described herein. It will be noted that alternative embodiments of the surgical instrument assembly and associated method of the present invention may not include all of the features described yet still benefit from at least some of the advantages of such features. Those of ordinary skill in the art may readily devise their own implementations of a surgical instrument assembly and associated method that incorporate one or more of the features of the present invention and fall within the spirit and scope of the present invention as defined by the appended claims.

What is claimed is:

1. A surgical assembly for preparing a tibia for implantation of a prosthetic implant, comprising:
   a tray trial adapted to be secured to a proximal end of said tibia, wherein (i) said tray trial includes a plate having a plate opening defined therein, and (ii) said plate opening has a center point;
   a first guide adapted to be secured to said tray trial, wherein (i) said first guide has a guide opening defined therein, and (ii) said guide opening has a first bushing-receiving portion and a second bushing-receiving portion which is distinct from said first bushing-receiving portion; and a drill bushing positionable in either said first bushing-receiving portion of said guide opening or said second bushing-receiving portion of said guide opening, wherein (i) said drill bushing has a bushing bore extending therethrough; (ii) said bushing bore having a center point; (iii) said center point of said bushing bore of said drill bushing is offset from said center point of said plate opening of said tray trial in a first direction when said drill bushing is positioned in said first bushing-receiving portion of said guide opening; and (iv) said center point of said bushing bore of said drill bushing is offset from said center point of said plate opening of said tray trial in a second direction when said drill bushing is positioned in said second bushing-receiving portion of said guide opening.

2. The surgical assembly of claim 1, wherein:

said guide opening of said first guide further has a first keying portion and a second keying portion, said drill bushing has a keying tab extending therefrom, said keying tab is positioned in said first keying portion of said guide opening when said drill bushing is positioned in said first bushing-receiving portion of said guide opening, and said keying tab is positioned in said second keying portion of said guide opening when said drill bushing is positioned in said second bushing-receiving portion of said guide opening.

3. The surgical assembly of claim 2, further comprising a punch which is adapted to be advanced through said guide opening of said first guide, wherein:

said punch includes a first cutting blade, a second cutting blade, and a third cutting blade, said guide opening of said first guide further has a blade-receiving portion, and during advancement of said punch through said guide opening (i) said first cutting blade of said punch is advanced through said first keying portion of said guide opening, (ii) said second cutting blade of said punch is advanced through said second keying portion of said guide opening, and (iii) said third cutting blade of said punch is advanced through said blade-receiving portion of said guide opening.

4. The surgical assembly of claim 1, wherein:

said first guide includes a guide body, said guide opening is defined in said guide body, said guide body includes a protrusion which extends into said guide opening at a location between said first bushing-receiving portion of said guide opening and said second bushing-receiving portion of said guide opening, and said protrusion prevents movement of said drill bushing between said first bushing-receiving portion of said guide opening and said second bushing-receiving portion of said guide opening without removal of said drill bushing from said guide opening.

5. The surgical assembly of claim 1, wherein:

said first guide includes a guide body, said guide opening is defined in said guide body, said guide body includes a protrusion which extends into said guide opening at a location between said first bushing-receiving portion of said guide opening and said second bushing-receiving portion of said guide opening, and said protrusion prevents sliding movement of said drill bushing between said first bushing-receiving portion of said guide opening and said second bushing-receiving portion of said guide opening.

6. The surgical assembly of claim 1, further comprising a second guide which is adapted to be secured to said tray trial, wherein:

said second guide has an elongated bore extending therethrough, said elongated bore has a center point, and said center point of said elongated bore is aligned with said center point of said plate opening of said tray trial when said second guide is secured to said tray trial.

7. The surgical assembly of claim 6, further comprising a bone drill, wherein:

said bone drill is advanced through said elongated bore of said second guide so as to drill a first hole in said tibia when said second guide is secured to said tray trial, and said bone drill is advanced through said bushing bore of said drill bushing so as to drill a second hole in said tibia when (i) said first guide is secured to said tray trial, and (ii) said drill bushing is positioned in either said first bushing-receiving portion of said guide opening or said second bushing-receiving portion of said guide opening.

8. The surgical assembly of claim 7, wherein said first hole drilled in said tibia is offset from said second hole drilled in said tibia.

9. A method of surgically preparing a tibia for implantation of a prosthetic implant, said method comprising the steps of:

securing a tray trial to a proximal end of said tibia, wherein (i) said tray trial includes a plate having a plate opening defined therein, and (ii) said plate opening has a center point;

securing a first guide to said tray trial, wherein (i) said first guide has a guide opening defined therein, and (ii) said guide opening has a first bushing-receiving portion and a second bushing-receiving portion which is distinct from said first bushing-receiving portion;

determining if a first drilled hole is to be offset in either a first direction or a second direction from said center point of said plate opening; and positioning a drill bushing in either said first bushing-receiving portion of said guide opening or said second bushing-receiving portion of said guide opening based on said determining step, wherein (i) said drill bushing has a bushing bore extending therethrough; (ii) said bushing bore has a center point; and (iii) said center point of said bushing bore of said drill bushing is offset from said center point of said plate opening of said tray trial when said drill bushing is positioned in either said first bushing-receiving portion of said guide opening or said second bushing-receiving portion of said guide opening.

10. The method of claim 9, further comprising the step of advancing a bone drill through said bushing bore of said drill bushing so as to drill said first drilled hole in said tibia subsequent to said positioning step.

11. The method of claim 10, wherein:

said guide opening of said first guide further has a first keying portion and a second keying portion, said drill bushing has a keying tab extending therefrom, said positioning step includes the step of positioning said keying tab of said drill bushing in either said first keying portion of said guide opening or said second keying portion of said guide opening based on said determining step.

12. The method of claim 11, further comprising the steps of:

removing said drill bushing from said guide opening of said first guide subsequent to said bone drill advancing step; and advancing a punch through said guide opening of said first guide so as to form a punched hole in said tibia, wherein said punch advancing step is performed subsequent to said removing step.

13. The method of claim 12, wherein:

said punch includes a first cutting blade, a second cutting blade, and a third cutting blade, said guide opening of said first guide further has a blade-receiving portion, and said punch advancing step includes the steps of (i) advancing said first cutting blade of said punch through said first keying portion of said guide opening, (ii) advancing said second cutting blade of said punch through said second keying portion of said guide opening, and (iii) advancing said third cutting blade of said punch through said blade-receiving portion of said guide opening.

14. The method of claim 9, further comprising the step of securing a second guide to said tray trial, wherein:

said second guide has an elongated bore extending therethrough, said elongated bore has a center point, and said center point of said elongated bore is aligned with said center point of said plate opening of said tray trial when said second guide is secured to said tray trial.

15. The method of claim 14, further comprising the step of advancing a bone drill through said elongated bore of said second guide so as to drill a second drilled hole in said tibia subsequent to said step of securing said second guide to said tray trial.

16. The method of claim 15, wherein said step of advancing said bone drill through said elongated bore of said second guide is performed prior to said step of securing said first guide to said tray trial.

17. The method of claim 9, further comprising the steps of:

advancing a bone drill through said bushing bore of said drill bushing so as to drill said first drilled hole in said tibia subsequent to said positioning step; and advancing a stem punch through said bushing bore of said drill bushing so as to punch an elongated punched hole in said tibia, wherein (i) said elongated punched hole is coaxial with said first drilled hole, and (ii) said stem punch advancing step is performed subsequent to said bone drill advancing step.

* * * * *